United States Patent [19]
Thomas

[11] Patent Number: 5,879,673
[45] Date of Patent: Mar. 9, 1999

[54] ADMINISTRATION OF THROMBOPOIETIN ON A SINGLE DAY ONLY

[75] Inventor: Griffith Roger Thomas, Burlingame, Calif.

[73] Assignee: Genentech, Inc., South San Francisco, Calif.

[21] Appl. No.: 697,631

[22] Filed: Aug. 28, 1996

Related U.S. Application Data

[63] Continuation-in-part of Ser. No. 591,925, Jan. 25, 1996, abandoned, and a continuation of Ser. No. 641,443, Apr. 29, 1996, abandoned.

[51] Int. Cl.$^6$ ................................................... A61K 38/19
[52] U.S. Cl. ................ 424/85.1; 424/192.1; 424/193.1; 435/69.5; 435/69.7; 530/351; 530/402
[58] Field of Search .................................... 530/351, 402; 435/69.1, 69.5, 172.1, 69.7; 424/85.1, 192.1, 193.1

[56] References Cited

U.S. PATENT DOCUMENTS

| | | | |
|---|---|---|---|
| 5,578,301 | 11/1996 | Myers | 424/85.1 |
| 5,593,666 | 1/1997 | McDonald | 424/85.1 |
| 5,627,267 | 5/1997 | Lyman | 530/351 |

OTHER PUBLICATIONS

M.M. Hokom et al., Blood 86(12):4486–4492, Dec. 15 1995.

T.R. Ulich et al., Blood 86(3):971–976, Aug. 1 1995.

K. Kaushansky et al., J. Clin. Invest. 96:1683–1687, Sep. 1995.

Ulich et al., "The Prolonged Hematologic Effects of a Single Injection of PEG–rHuMGDF is Normal in Thrombocytopenic Mice," (Abstract No. 1399) *Blood*, 88:335a (1996). (Nov.).

Shibuya et al., "Single Injection of Pegylated Recombinant Human Megakaryocyte Growth and Development Factor (PEG–rHuMGDF) Promotes Hematologic Recovery in Irradiated Mice," (Abstract No. 1400) *Blood*, 88:335a (1996). (Nov.).

*Primary Examiner*—Lorraine Spector
*Attorney, Agent, or Firm*—Timothy R. Schwartz; Daryl B. Winter

[57] ABSTRACT

The present invention is directed to the surprising and unexpected finding that biologically active thrombopoietin materials can be administered with substantial therapeutic effect at dosage rates commensurate with previously reported administration of such materials, but in a single or low-multiple daily administration. Thus, the predicate of the present invention relates to the reversal of thrombocytopenia by administering to a patient having or in need of such treatment a single or low-multiple daily dose of a therapeutically effective amount of a thrombopoietin. The preferable dose of the active material ranges from about 1 to about 10 $\mu$g/kg body weight.

23 Claims, 7 Drawing Sheets

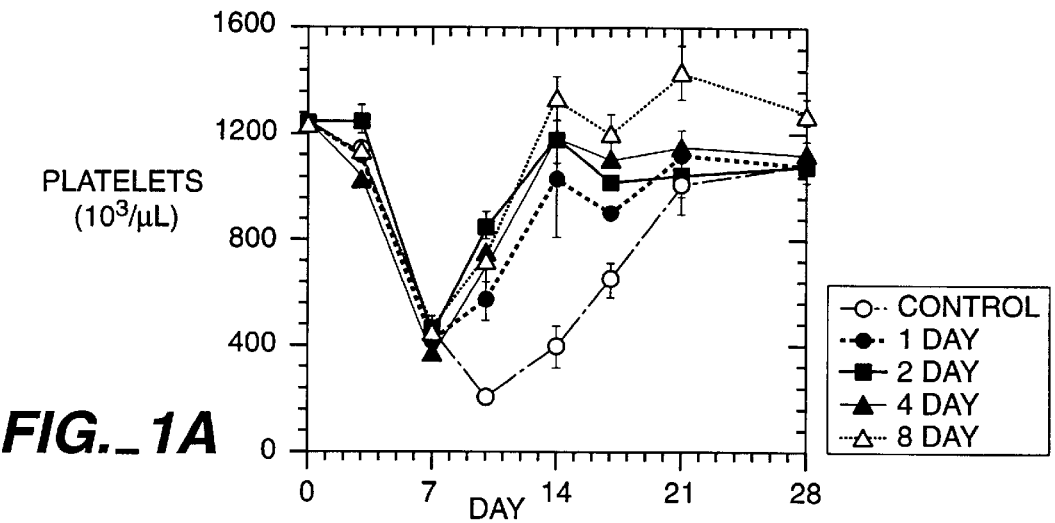
FIG._1A
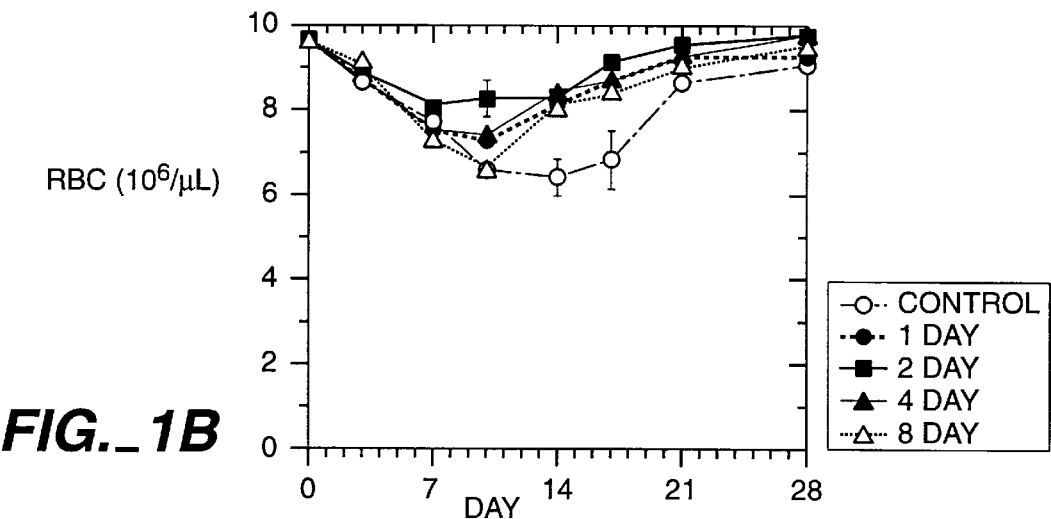
FIG._1B
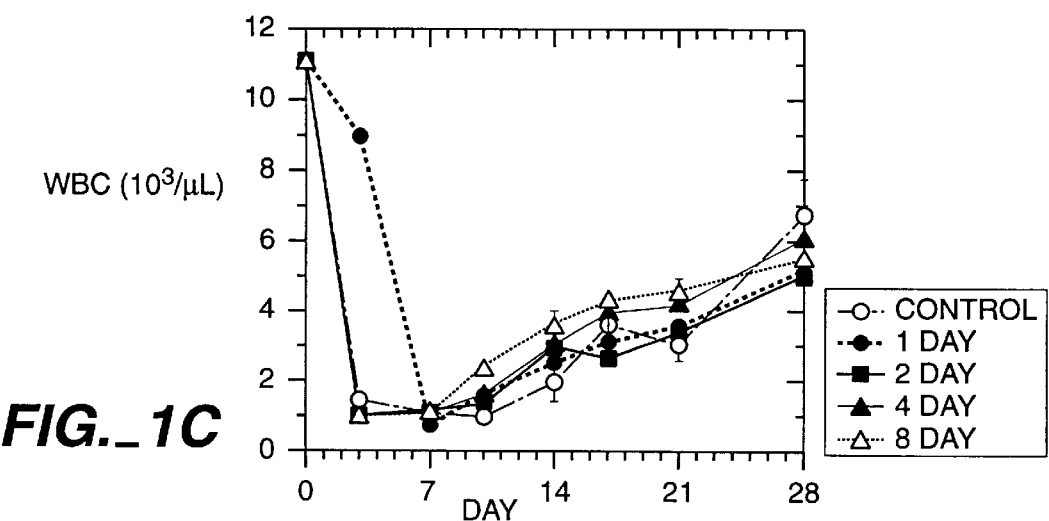
FIG._1C

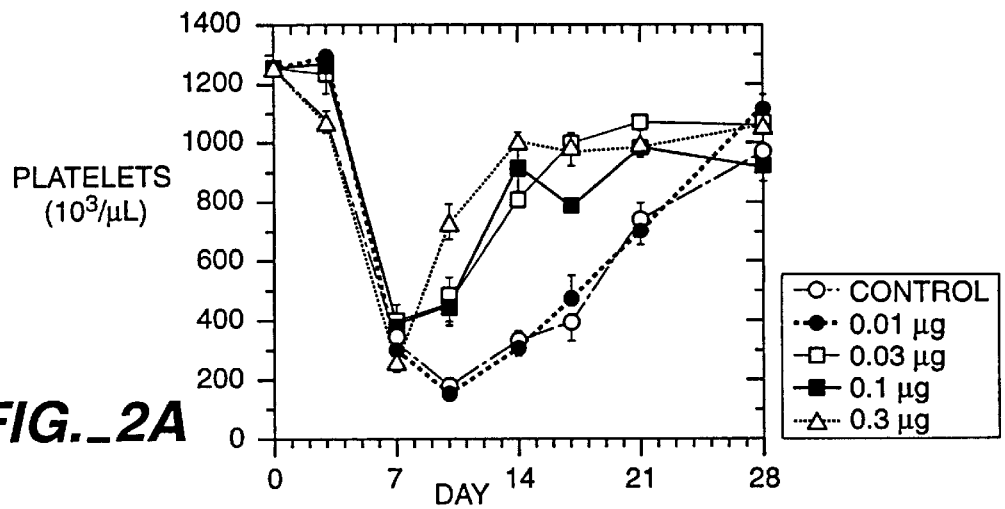
FIG._2A
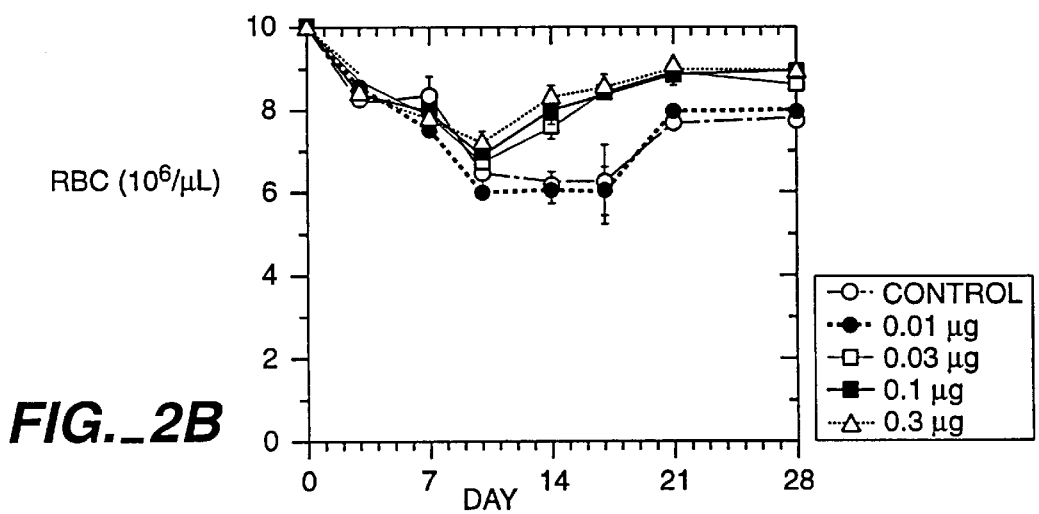
FIG._2B
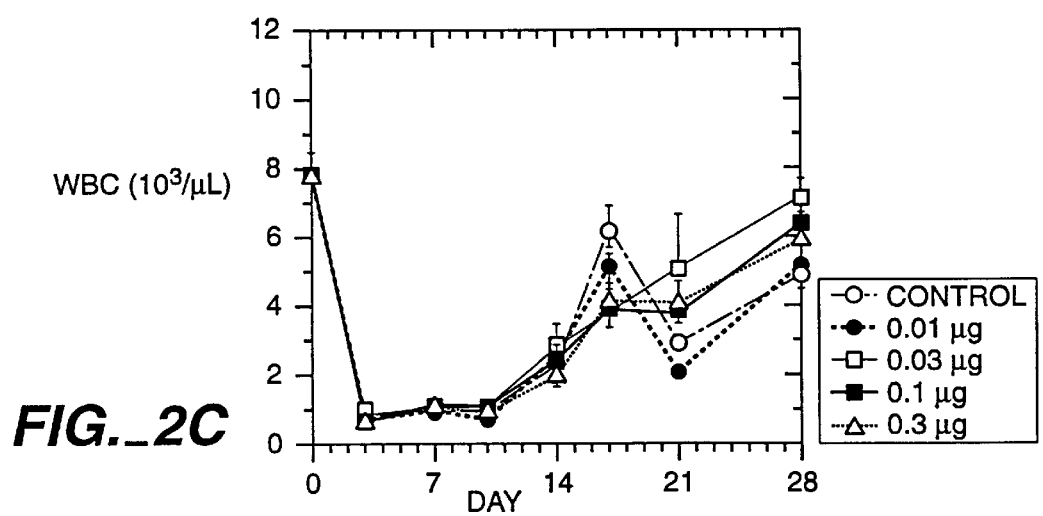
FIG._2C

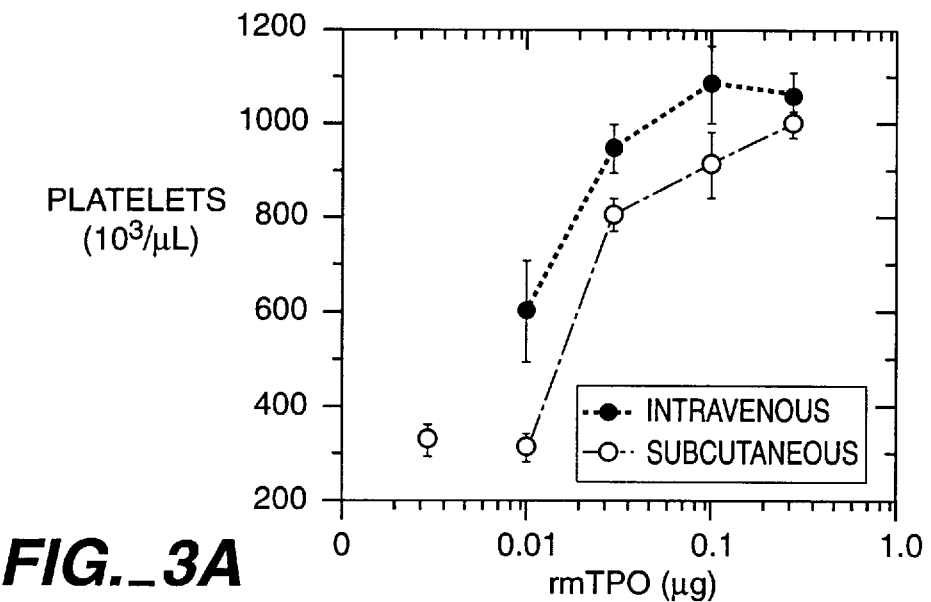
*FIG._3A*
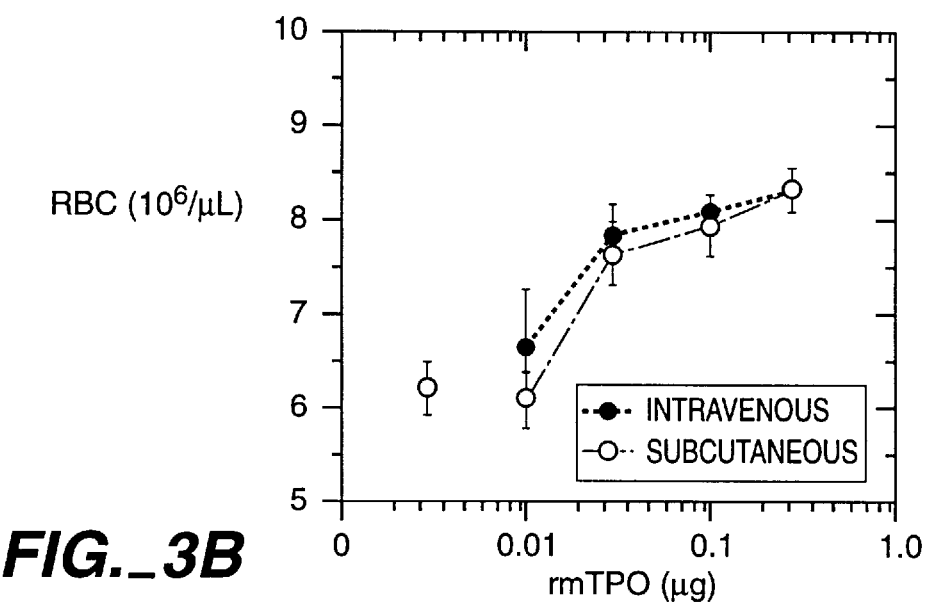
*FIG._3B*

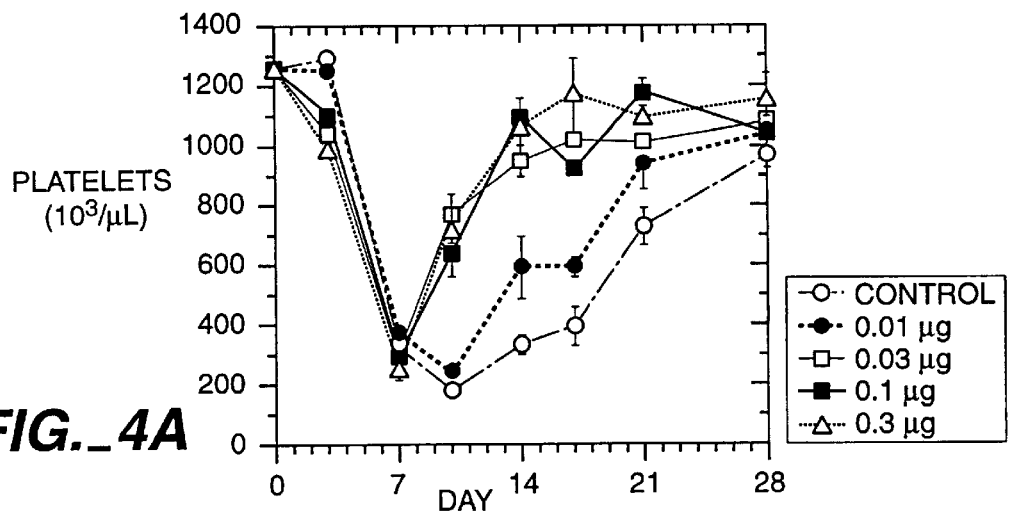
FIG._4A
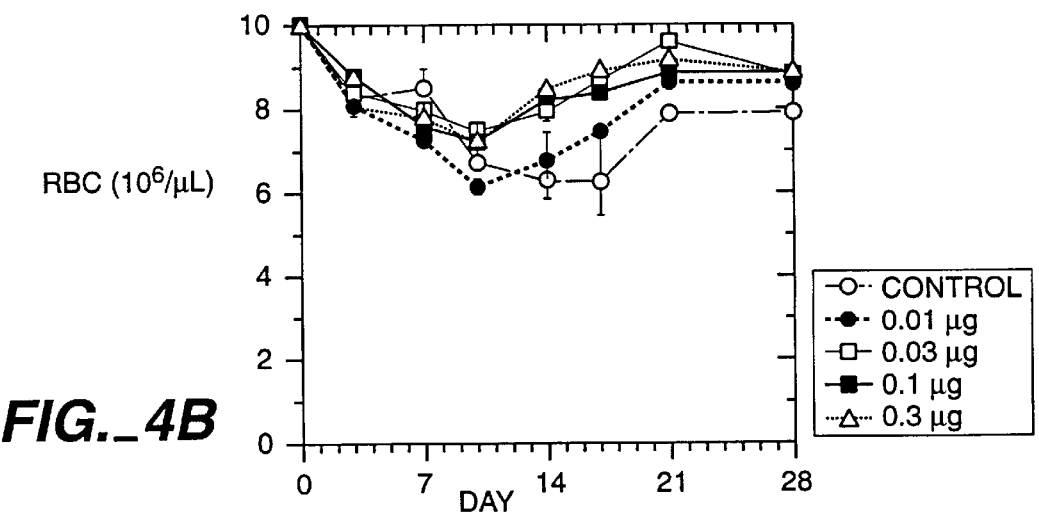
FIG._4B
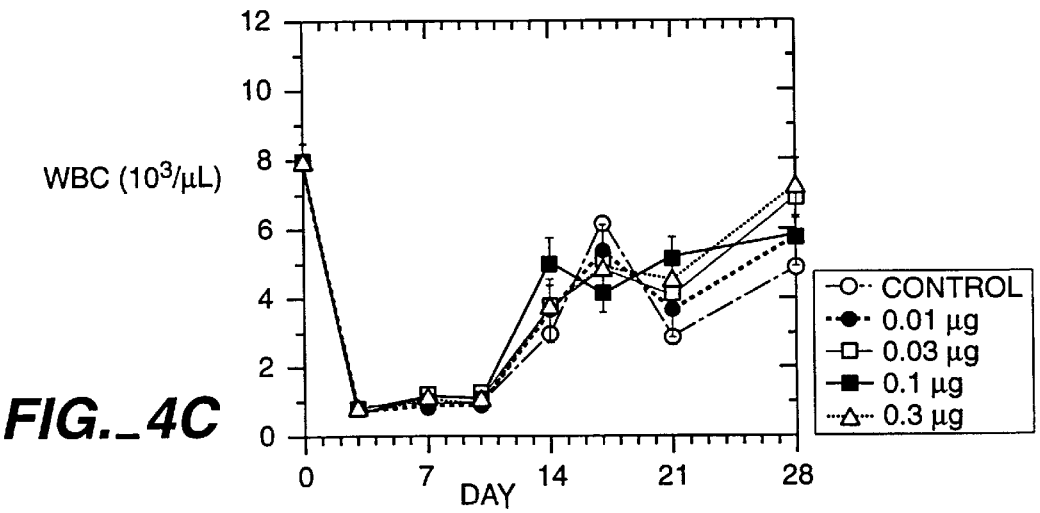
FIG._4C

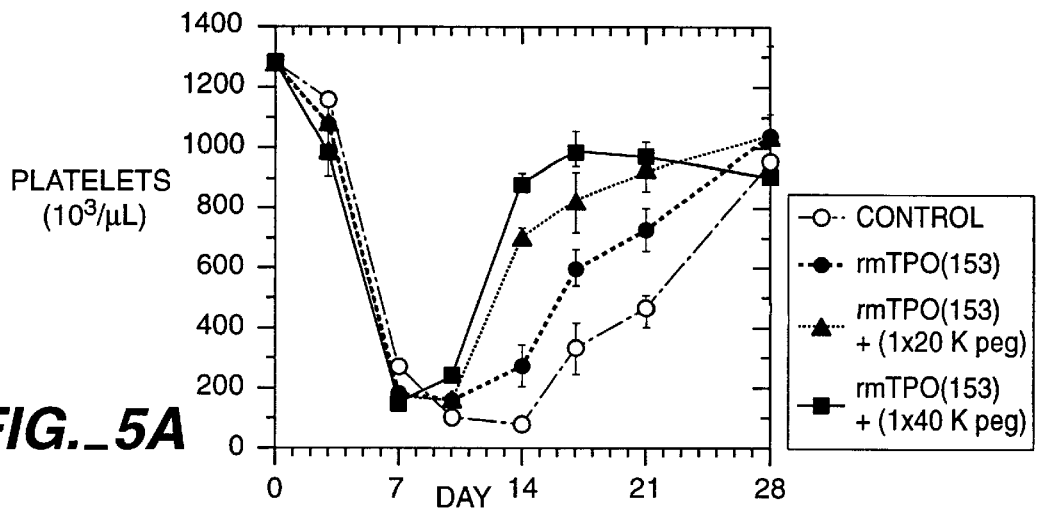
FIG._5A
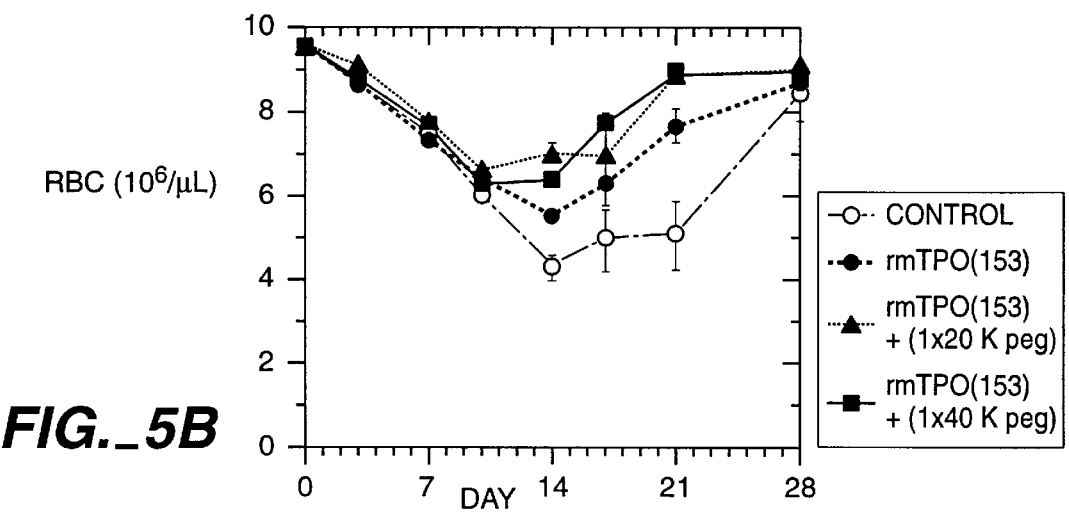
FIG._5B
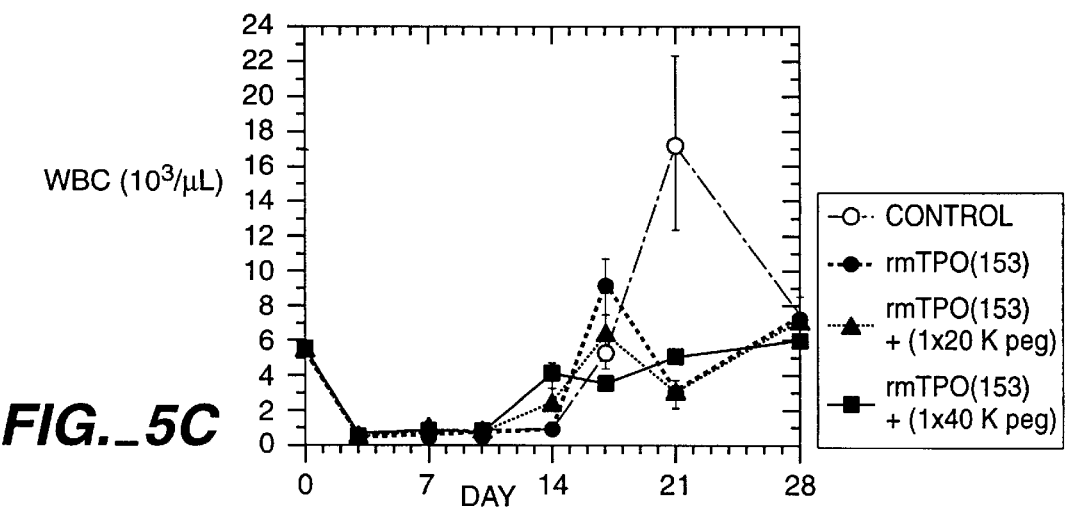
FIG._5C

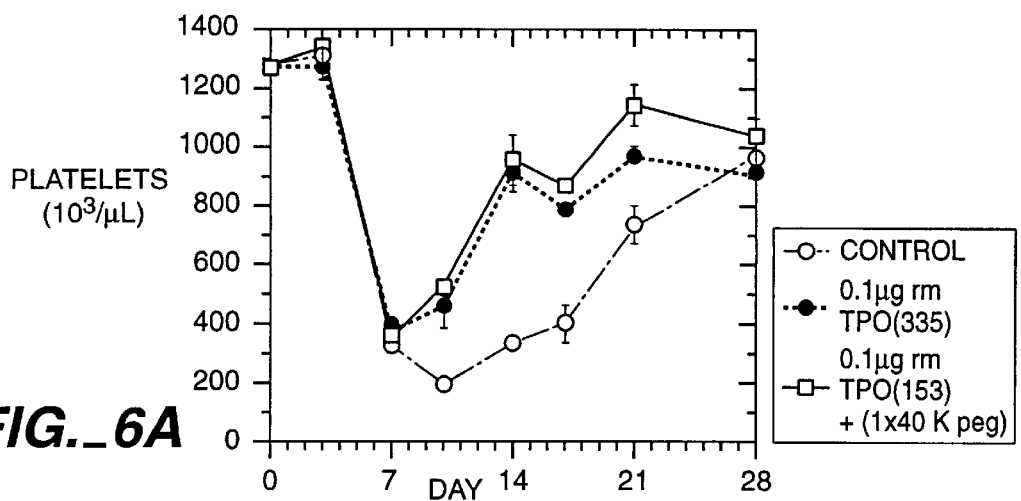
FIG._6A
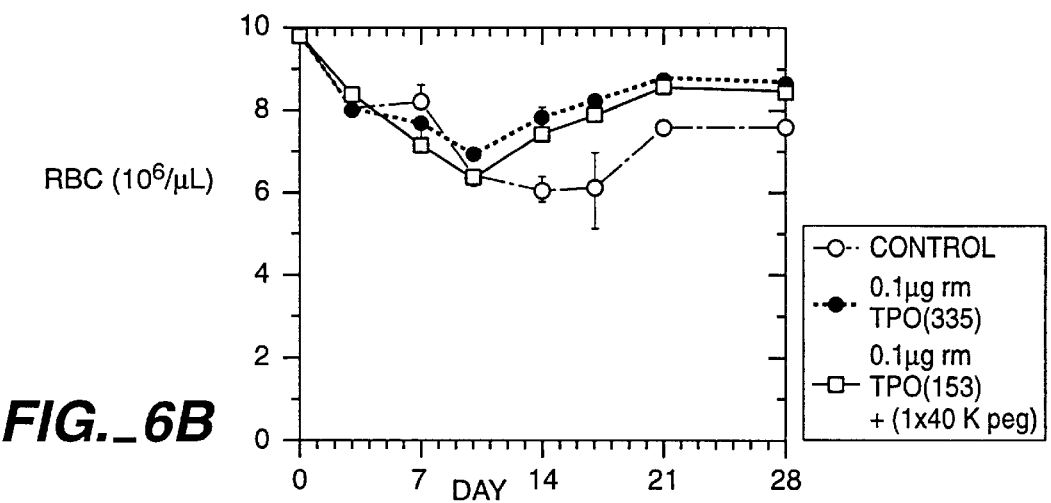
FIG._6B
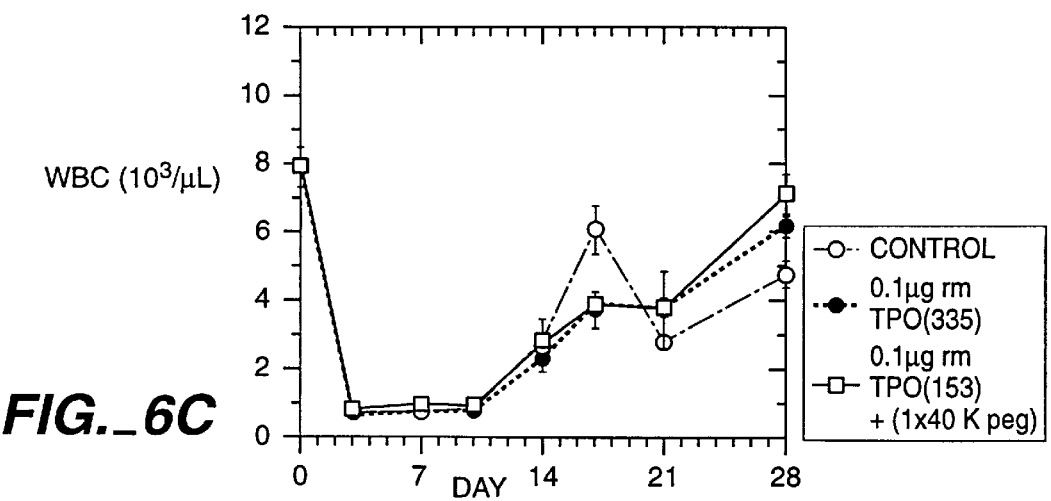
FIG._6C

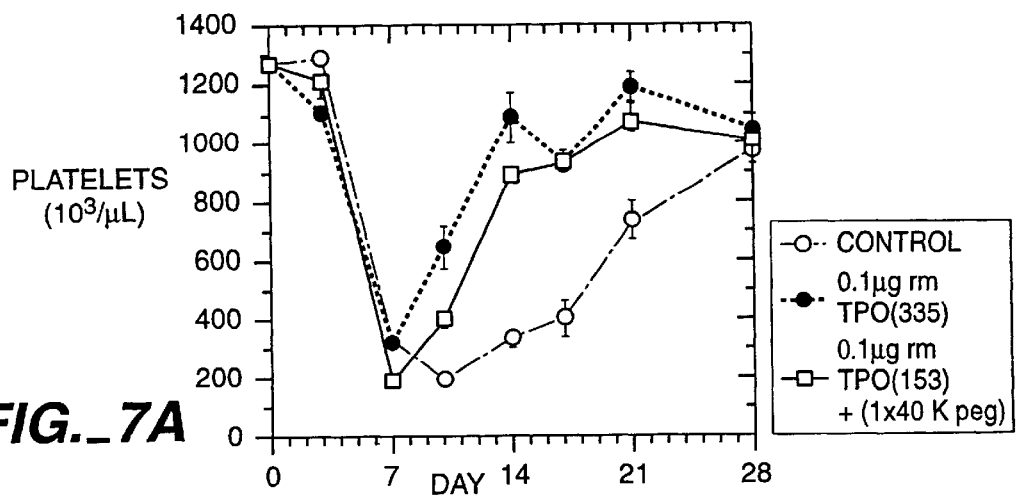
FIG._7A
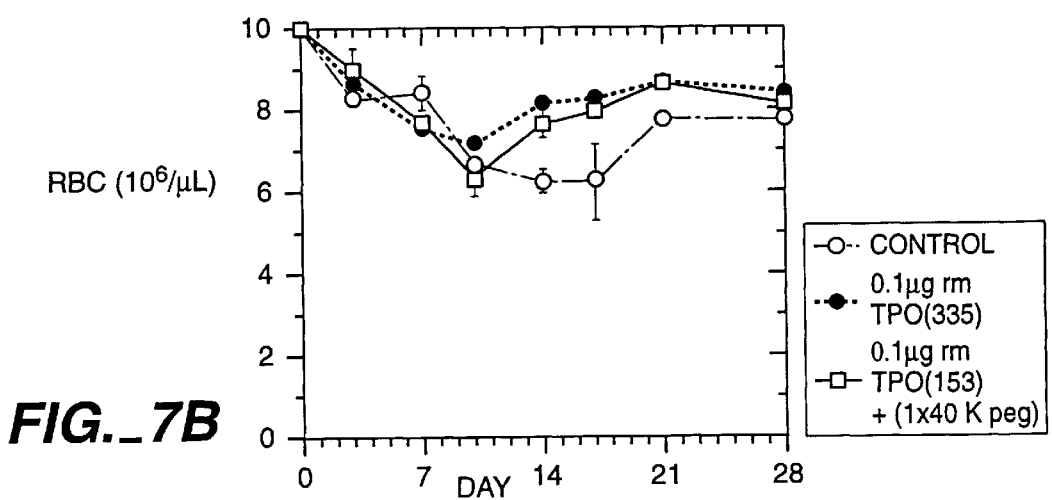
FIG._7B
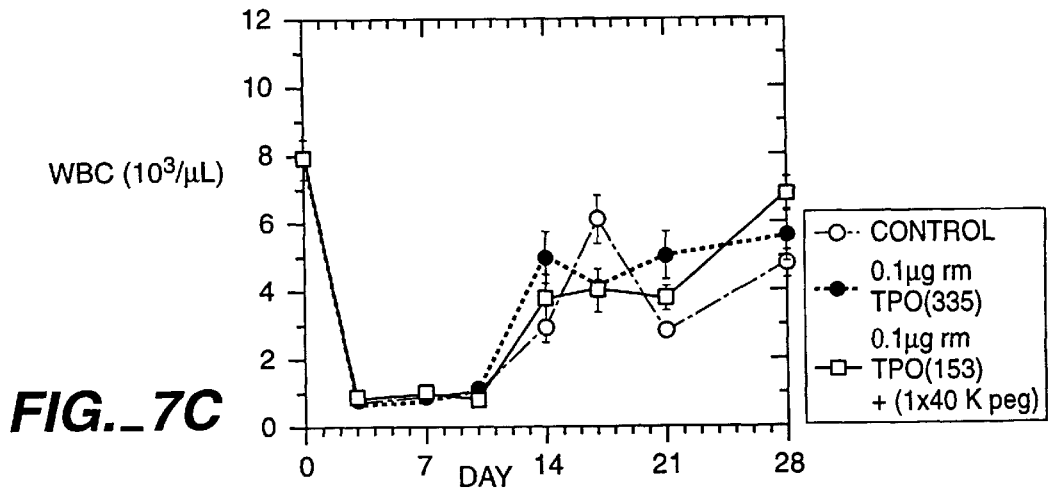
FIG._7C

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 32 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:1:

ATCGATATCG ATCAGCCAGA CACCCCGGCC AG						32

( 2 ) INFORMATION FOR SEQ ID NO:2:

( i ) SEQUENCE CHARACTERISTICS:
        ( A ) LENGTH: 36 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:2:

GCTAGCTCTA GACAGGGAAG GGAGCTGTAC ATGAGA						36

( 2 ) INFORMATION FOR SEQ ID NO:3:

( i ) SEQUENCE CHARACTERISTICS:
        ( A ) LENGTH: 35 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:3:

TCTAGATCTA GATCACCTGA CGCAGAGGGT GGACC						35

( 2 ) INFORMATION FOR SEQ ID NO:4:

( i ) SEQUENCE CHARACTERISTICS:
        ( A ) LENGTH: 31 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:4:

ATCGATATCG ATAGCCAGAC ACCCCGGCCA G						31

( 2 ) INFORMATION FOR SEQ ID NO:5:

( i ) SEQUENCE CHARACTERISTICS:
        ( A ) LENGTH: 33 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:5:

AGTCGACGTC GACGTCGGCA GTGTCTGAGA ACC						33

( 2 ) INFORMATION FOR SEQ ID NO:6:

( i ) SEQUENCE CHARACTERISTICS:
        ( A ) LENGTH: 36 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:6:

AGTCGACGTC GACTCACCTG ACGCAGAGGG TGGACC						36

( 2 ) INFORMATION FOR SEQ ID NO:7:

( i ) SEQUENCE CHARACTERISTICS:
    ( A ) LENGTH: 62 base pairs
    ( B ) TYPE: Nucleic Acid
    ( C ) STRANDEDNESS: Single
    ( D ) TOPOLOGY: Linear ( i i ) MOLECULE TYPE: DNA (genomic)

( x i ) SEQUENCE DESCRIPTION: SEQ ID NO:7:

```
CGCGTATGCC AGCCCGGCTC CTCCTGCTTG TGACCTCCGA GTCCTCAGTA        50

AACTGCTTCG TG                                                 62
```

( 2 ) INFORMATION FOR SEQ ID NO:8:

( i ) SEQUENCE CHARACTERISTICS:
        ( A ) LENGTH: 61 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:8:

```
AGTCACGAAG CAGTTTACTG AGGACTCGGA GGTCACAAGC AGGAGGAGCC        50

GGGCTGGCAT A                                                  61
```

( 2 ) INFORMATION FOR SEQ ID NO:9:

( i ) SEQUENCE CHARACTERISTICS:
        ( A ) LENGTH: 37 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:9:

```
CTAGAATTAT GAAAAGAAT ATCGCATTTC TTCTTAA                       37
```

( 2 ) INFORMATION FOR SEQ ID NO:10:

( i ) SEQUENCE CHARACTERISTICS:
        ( A ) LENGTH: 37 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:10:

```
CGCGTTAAGA AGAAATGCGA TATTCTTTTT CATAATT                      37
```

( 2 ) INFORMATION FOR SEQ ID NO:11:

( i ) SEQUENCE CHARACTERISTICS:
        ( A ) LENGTH: 66 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:11:

```
CTAGAATTAT GAAAAGAAT ATCGCATTTC ATCACCATCA CCATCACCAT         50

CACATCGAAG GTCGTA                                             66
```

( 2 ) INFORMATION FOR SEQ ID NO:12:

(  i ) SEQUENCE CHARACTERISTICS:
   ( A ) LENGTH: 64 base pairs
   ( B ) TYPE: Nucleic Acid
   ( C ) STRANDEDNESS: Single
   ( D ) TOPOLOGY: Linear ( i i ) MOLECULE TYPE: DNA (genomic)

( x i ) SEQUENCE DESCRIPTION: SEQ ID NO:12:

TACGACCTCG ATGTGATGGT GATGGTGATG GTGATGAAAT GCGATATTCT          50

TTTTCATAAT TCCG          64

( 2 ) INFORMATION FOR SEQ ID NO:13:

( i ) SEQUENCE CHARACTERISTICS:
      ( A ) LENGTH: 65 base pairs
      ( B ) TYPE: Nucleic Acid
      ( C ) STRANDEDNESS: Single
      ( D ) TOPOLOGY: Linear ( i i ) MOLECULE TYPE: DNA (genomic)

( x i ) SEQUENCE DESCRIPTION: SEQ ID NO:13:

CTAGAATTAT GAAAAGAAT ATCGCATTTC ATCACCATCA CCATCACCAT          50

CACATCGAAC CACGT          65

( 2 ) INFORMATION FOR SEQ ID NO:14:

( i ) SEQUENCE CHARACTERISTICS:
      ( A ) LENGTH: 66 base pairs
      ( B ) TYPE: Nucleic Acid
      ( C ) STRANDEDNESS: Single
      ( D ) TOPOLOGY: Linear ( i i ) MOLECULE TYPE: DNA (genomic)

( x i ) SEQUENCE DESCRIPTION: SEQ ID NO:14:

TACGTGGTTC GATGTGATGG TGATGGTGAT GGTGATGAAA TGCGATATTC          50

TTTTTCATAA TTCCGA          66

( 2 ) INFORMATION FOR SEQ ID NO:15:

( i ) SEQUENCE CHARACTERISTICS:
      ( A ) LENGTH: 19 base pairs
      ( B ) TYPE: Nucleic Acid
      ( C ) STRANDEDNESS: Single
      ( D ) TOPOLOGY: Linear ( i i ) MOLECULE TYPE: DNA (genomic)

( x i ) SEQUENCE DESCRIPTION: SEQ ID NO:15:

TCCACCCTCT GCGTCAGGT          19

( 2 ) INFORMATION FOR SEQ ID NO:16:

( i ) SEQUENCE CHARACTERISTICS:
      ( A ) LENGTH: 18 base pairs
      ( B ) TYPE: Nucleic Acid
      ( C ) STRANDEDNESS: Single
      ( D ) TOPOLOGY: Linear ( i i ) MOLECULE TYPE: DNA (genomic)

( x i ) SEQUENCE DESCRIPTION: SEQ ID NO:16:

AGCTACCTGA CGCAGAGG          18

( 2 ) INFORMATION FOR SEQ ID NO:17:

( i ) SEQUENCE CHARACTERISTICS:
        ( A ) LENGTH: 62 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:17:

GCAGCAGTTC TAGAATTATG TCNCCNGCNC CNCCNGCNTG TGACCTCCGA     50

ACACTGGAGG CT     62

( 2 ) INFORMATION FOR SEQ ID NO:18:

( i ) SEQUENCE CHARACTERISTICS:
        ( A ) LENGTH: 49 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:18:

GAAGGACATG GGAGTCACGA AGCAGTTTAC TGAGAACAAA TGACTCTTG     49

( 2 ) INFORMATION FOR SEQ ID NO:19:

( i ) SEQUENCE CHARACTERISTICS:
        ( A ) LENGTH: 45 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:19:

CTAGAATTAT GAAAAAGAAT ATCGCATTTA TCGAAGGTCG TAGCC     45

( 2 ) INFORMATION FOR SEQ ID NO:20:

( i ) SEQUENCE CHARACTERISTICS:
        ( A ) LENGTH: 38 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:20:

TACGACCTTC GATAAATGCG ATATTCTTTT TCATAATT     38

( 2 ) INFORMATION FOR SEQ ID NO:21:

( i ) SEQUENCE CHARACTERISTICS:
        ( A ) LENGTH: 45 base pairs
        ( B ) TYPE: Nucleic Acid
        ( C ) STRANDEDNESS: Single
        ( D ) TOPOLOGY: Linear ( i i ) MOLECULE TYPE: DNA (genomic)

( x i ) SEQUENCE DESCRIPTION: SEQ ID NO:21:

CTAGAATTAT GAAAAAGAAT ATCGCATTTC TTCTTAAACG TAGCC     45

( 2 ) INFORMATION FOR SEQ ID NO:22:

( i ) SEQUENCE CHARACTERISTICS:

(A) LENGTH: 38 base pairs
(B) TYPE: Nucleic Acid
(C) STRANDEDNESS: Single
(D) TOPOLOGY: Linear (ii) MOLECULE TYPE: DNA (genomic)

(xi) SEQUENCE DESCRIPTION: SEQ ID NO:22:

TACGTTTAAG AAGAAATGCG ATATTCTTTT TCATAATT                         38

ADMINISTRATION OF THROMBOPOIETIN ON A SINGLE DAY ONLY

CROSS-REFERENCE TO RELATED APPLICATIONS

This is a continuation-in-part of U.S. Ser. No. 08/591,925 filed 25 Jan. 1996, abandoned, and a continuation of U.S. Ser. No. 08/641,443 filed 29 Apr. 1996, abandoned.

The present application, and the subject matter contained therein, is related to the following patent applications and their contents: International Patent Application PCT/US94/14553, filed 28 Dec. 1994 (published under number WO95/18858 on 13 Jul. 1995) and the several patent applications referenced therein, namely, U.S. Ser. No. 08/176,553, filed 3 Jan. 1994; 08/185,607, filed 21 Jan. 1994; 08/196,689 filed 15 Feb. 1994; 08/223,263 filed 4 Apr. 1994; 08/249,376 filed 25 May 1994; 08/348,657 filed 2 Dec. 1994 and 08/348,658 filed 2 Dec. 1994.

FIELD OF THE INVENTION

The present invention relates to a new method of using thrombopoietin, and biologically active derivatives and isoforms thereof, for the treatment of immune and/or hematopoietic disorders including thrombocytopenia. The use contemplates the co-administration of such materials together with a cytokine, especially a colony stimulating factor or interleukin. The use includes and is included within a method for treating a mammal having or at risk for thrombocytopenia by administering to said mammal in need of such treatment a therapeutically effective amount of said material(s).

BACKGROUND OF THE INVENTION

The hematopoietic system produces the mature highly specialized blood cells known to be necessary for survival of all mammals. These mature cells include erythrocytes, specialized to transport oxygen and carbon dioxide, T- and B-lymphocytes, responsible for cell- and antibody-mediated immune responses, platelets or thrombocytes, specialized to form blood clots, and granulocytes and macrophages, specialized as scavengers and as accessory cells to combat infection. All of these specialized mature blood cells are derived from a single common primitive cell type referred to as the pluripotent stem cell found primarily in bone marrow.

The mature highly specialized blood cells must be produced in large numbers continuously throughout the life of a mammal. The vast majority of these specialized blood cells are destined to remain functionally active for only a few hours to weeks. Thus, continuous renewal of these mature blood cells, the primitive stem cells themselves, as well as any intermediate or lineage, committed progenitor cell lines lined between the primitive and mature cells, is necessary in order to maintain the normal steady state blood cell needs for continued life of the mammal.

At the heart of the hematopoietic system lies the pluripotent stem cell(s). These cells are relatively few in number and undergo self-renewal by proliferation to produce daughter stem cells, or they are transformed in a series of differentiation steps into increasingly mature lineage-restricted progenitor cells, ultimately forming the highly specialized mature blood cell(s).

The underlying principal of the normal hematopoietic cell system appears to be decreased capacity for self-renewal as multipotency is lost and lineage-restriction and maturity is acquired. Thus, at one end of the hematopoietic cell spectrum lies the pluripotent stem cell possessing the capacity for self-renewal and differentiation into all the various lineage-specific committed progenitor cells. At the other end of the spectrum lie the highly lineage-restricted progenitors and their progeny which have lost the ability of self renewal but have acquired mature functional activity.

The proliferation and development of stem cells and lineage-restricted progenitor cells are carefully controlled by a variety of hematopoietic growth factors or cytokines. Thus, hematopoietic growth factors may influence growth and differentiation of one or more lineages, may overlap with other growth factors in affecting a single progenitor cell-line, or may act synergistically with other factors.

It will be appreciated from the foregoing that novel hematopoietic growth factors that effect survival, proliferation, differentiation or maturation of any of the blood cells or predecessors thereof would be useful, especially to assist in the re-establishment of a diminished hematopoietic system caused by disease or after radiation- or chemo-therapy.

Platelets are critical elements of the blood clotting mechanism. Depletion of the circulating level of platelets, called thrombocytopenia, occurs and is manifested in various clinical conditions and disorders. Clinical thrombocytopenia is commonly defined as a condition wherein the platelet count is below about $150 \times 10^9$ per liter. The major causes of thrombocytopenia can be broadly divided into three categories on the basis of platelet life span, namely: 1) impaired production of platelets by the bone marrow, e.g., thrombocytopenia brought about by chemo- and radiation-therapy, 2) platelet sequestration in the spleen (splenomegaly) and 3) increased destruction of platelets in the peripheral circulation, e.g., thrombocytopenia brought about by autoimmune disorders. Additionally, in patients receiving large volumes of rapidly administered platelet-poor blood products, thrombocytopenia may develop due to dilution factors. A more detailed description of thrombocytopenia and its causes, may be found in Schafner, "Thrombocytopenia and Disorders of Platelet Disfunction", *Internal Medicine*, John J. Hutton et al. Eds., Little, Brown & Co., Boston/Toronto/London, Third Ed. (1990) as well as International Patent Application No. PCT/US94/14553 (International Publication No. WO95/18858), referred to supra.

The therapeutic approach to the treatment of patients with thrombocytopenia is dictated by the severity and urgency of the clinical situation. The treatment is similar for HIV-associated and non-HIV-related thrombocytopenia, and although a number of different therapeutic approaches have been used, the therapy remains clinically controversial.

It will be appreciated from the foregoing that one way to treat thrombocytopenia would be to obtain an agent capable of accelerating the differentiation and maturation of megakaryocytes or precursors thereof into the platelet-producing form. Considerable efforts have been expended on identifying such an agent. One commonly referred to is thrombopoietin (TPO), the subject of the present application. Other names for TPO commonly found in the literature at this time include: thrombocytopoiesis stimulating factor (TSF); megakaryocyte colony-stimulating factor (MK-CSF), megakaryocyte growth and development factor, megakaryocyte stimulating factor, megakaryocyte potentiator and mpl ligand.

The cited International Patent Application PCT/US94/14553 describes the identification, isolation, production and use of an isolated mammalian megakaryocytopoietic proliferation and maturation promoting protein denominated the "MPL ligand" (ML), or more commonly, "thrombopoietin" (TPO), which has been found capable of stimulating proliferation, maturation and/or differentiation of megakaryocytes into the mature platelet-producing form.

Attention is directed as well to International Patent Application Publications Nos. WO95/26746, WO95/21919 and WO95/21920.

The PCT/US94/14553 application includes various aspects of associated embodiments of TPO, including a method of treating a mammal having or at risk for a hematopoietic disorder, notably thrombocytopenia, comprising administering a therapeutically effective amount of TPO materials to the mammal. Optionally, TPO is administered as such or in combination with a cytokine, especially a colony stimulating factor or interleukin. For purposes disclosed in said International Patent Application, TPO is broadly defined as including TPO itself or various variants, derivatives or isoforms thereof, including fragments that share at least one biological property in common with intact TPO for the treatment of thrombocytopenia. "Biological property", when used in conjunction with the definition of the various TPO materials useful as described in said patent application, means that they have thrombopoietic activity or an in vivo effector or antigenic function or activity that is directly or indirectly caused or performed by the TPO material.

With respect to the therapeutic use of thrombopoietin materials, as described in said International Patent Application No. PCT/US94/14553, the TPO materials are therein described for administration in admixture with a pharmaceutically acceptable carrier via any of several administrative modes. The daily regimen is described as ranging from about 0.1 to 100 $\mu$g/kg body weight, preferably from about 0.1 to 50 $\mu$g/kg body weight, preferably at an initial dosage ranging from about 1 to 5 $\mu$g/kg per day. Implicit within the teachings of said patent application is a regimen of administering such a dosage rate over a period of several to many days following a projected or actual state of reduced platelet count.

Published clinical studies of clinically administered thrombopoietin indicates a dosage and administration regimen consisting of the administration of thrombopoietin, subcutaneously at dosages of 0.03 to 5.0 $\mu$g/kg body weight once per day over a period of ten days for a condition marked by thrombocytopenia. See Abstract 1977, Blood 86 (1995). See also Abstracts 1012, 1014 and 1978, Blood 86 (1995).

Likewise, the compound epoetin alfa, which is a given name for erythropoietin (marketed as Epogen by Amgen, Inc.), is a glycoprotein indicated for stimulation of red blood cell production. It is indicated in a dosage and administration regimen consisting of starting doses over a range of 150 to 300 units per kg three times weekly for a period of many weeks in order to stimulate the proliferation of red blood cells in patients suffering from a depletion however realized.

Filgastrim, marketed as Neupogen by Amgen, Inc., is a granulocyte colony stimulating factor (G-CSF). Its indicated regimen is the administration of from 5 to 10 $\mu$g/kg subcutaneously daily for two weeks.

Based upon this anecdotal evidence, the conventional regimen in administering materials for the proliferation of red blood cells or other primary blood cells to reverse the effects of thrombocytopenia, is continuous administration of therapeutically effective amounts of the biological material daily over a period of many days to patients in need of such therapy following an episode resulting in thrombocytopenia.

For convenience to physicians and especially patients alike, there exists an objective of developing alternative dosage/administration regimens of such biological materials that would be advantageous and therapeutically equivalent or superior to reverse the effects of thrombocytopenia.

SUMMARY OF THE INVENTION

The present invention is based upon the unexpected and surprising finding that biologically active thrombopoietin materials can produce therapeutic effect by administering a single or low-multiple daily dose of a therapeutically effective amount to a patient having or in need of treatment for thrombocytopenia.

Thus, the present invention in its basic aspect is directed to a method of treating a mammal having or at risk for thrombocytopenia comprising administering to a mammal in need of such treatment a single or low-multiple daily dose of a therapeutically effective amount of a thrombopoietin. In its preferred aspect the present invention is directed to the single administration of a therapeutically effective amount.

By the term "low-multiple" in connection with the dosing is meant the administration of multiple doses of therapeutically effective amounts over a short period of time which is, and has been found to be herein, independent of the onset of therapeutic response, i.e., increased platelet production/levels. Thus, as a fundamental predicate, the present invention is directed to the mere single administration of a therapeutically effective amount of a thrombopoietin. It has been found that such a single administration produces a therapeutic effect equivalent to that realized when a therapeutically effective amount of the same material is administered over the conventional multiple many day regimen suggested and taught by the extant art.

It will be understood that although a single administration of a thrombopoietin to a patient has been found to be therapeutically effective for the treatment of thrombocytopenia, it can be appreciated that a low-multiple (daily) regimen may be employed, but without appreciable or significant therapeutic significance apart from the obvious clinical disadvantages. It has been found herein that a single dose stimulates the onset of therapeutic response, and although multiple dosing is contemplated herein, perhaps dictated by clinical conditions and practice, termination of dosing after a single or low-multiple administration is independent of therapeutic response.

It has been found in accord with the present invention that the single or low multiple administration regimen of the present invention is effective at relatively low dosage rates of the order of about 0.1 to 10, preferably about 0.3 to 10, more preferably about 0.5 to 10, still more preferably about 0.5 to 5 $\mu$g/kg body weight of the patient. In single dosing, preferred would be the total administration of about 2±1.5 $\mu$g/kg of body weight. In low-multiple dosing, preferred would be the administration of from about 0.5 to 1.5 $\mu$g/kg body weight per dose. The above dosages are predicated on preferred intravenous administration. In administration via the subcutaneous route, the total amount administered would be in the range of about one to three times the amount administered via the intravenous route, preferably about two times.

The optimal dosage rate and regimen will be determined by the attending physician taking into consideration various factors known to modify the action of drugs including severity and type of disease, body weight, sex, diet, time and route of administration, other medications and other relevant clinical factors. In accordance with the present invention the regimen of the present invention will consist of a single or low-multiple administration of a thrombopoietin material hereof in the broad range of from about 0.1 to 100 µg/kg body weight, preferably a dosage within the range of from about 0.1 to 50 µg/kg body weight. Most preferably, the present invention is predicated on the unexpected result that a single or low-multiple administration of a dosage ranging from about 0.1 to about 1.0 or more preferably about 0.5 to about 5 µg/kg produces a therapeutic effect that is therapeutically equivalent to the administration of the same amount of material or more over a regimen spanning daily administration over a number of days upwards of a week or more.

The biologically active thrombopoietin materials of the present invention can be administered, in accord herewith, in various routes including via the nose or lung, subcutaneously, and preferably intravenously. In all events, depending upon the route of administration, the biologically active thrombopoietin materials of the present invention are preferably administered in combination with an appropriate pharmaceutically acceptable carrier or excipient. When administered systemically, the therapeutic composition should be pyrogen-free and in a parenterally acceptable solution having due regard for physiological pH isotonicity and stability. These conditions are generally well known and accepted to those of skill in the appropriate art.

Briefly, dosage formulations of the materials of the present invention are prepared for storage or administration by mixing the compound having the desired degree of purity with physiologically acceptable carriers, excipients and/or stabilizers. Such materials are non-toxic to the recipients at the dosages and concentrations employed and include buffers such as phosphate, citrate, acetate and other organic acid salts; antioxidants such as ascorbic acid; low molecular weight peptides such as polyarginine, proteins such as serum albumen, gelatin or immunoglobulins; hydrophilic polymers such as polyvinylpyrrolidinone; amino acids such as glycine, glutamic acid, aspartic acid or arginine; monosaccharides, disaccharides and other carbohydrates including cellulose or its derivatives, glucose, mannose or dextrins; chelating agents such as EDTA; sugar alcohol such as mannitol or sorbitol; counter-ions such as sodium and/or non-ionic surfactants such as Tween, Pluronics or polyethylineglycol.

The biologically active thrombopoietin materials hereof can be administered as the free acid or base form or as a pharmaceutically acceptable salt and are compounded with a physiologically acceptable vehicle, carrier, excipient, binder, preservative, stabilizer, flavoring agent, etc. as called for by accepted pharmaceutical practice.

Sterile compositions for injection can be formulated according to conventional pharmaceutical or pharmacological practice. For example, dissolution or suspension of the active material in a vehicle such as water or naturally occurring vegetable oil like sesame, peanut, or cottonseed oil or a synthetic fatty vehicle like ethyloleate or the like may be desired. Again, buffers, preservatives, anti-oxidants and the like can be incorporated according to accepted pharmaceutical practice. The biologically active thrombopoietin materials of the present invention may be employed alone or administered in combination with other cytokines, hematapoietins, interleukins, growth factors, or antibodies in the treatment of the above identified disorders and conditions marked by thrombocytopenia. Thus, the present active materials may be employed in combination with other protein or peptide having thrombopoietic activity including: G-CSF, GM-CSF, LIF, M-CSF, IL-2, IL-3, erythropoietin (EPO), Kit ligand, IL-6, IL-11, FLT-3 ligand, and so forth.

Suitable examples of sustained-release preparations include semipermeable matrices of solid hydrophobic polymers containing the polypeptide, which matrices are in the form of shaped articles, e.g. films, or microcapsules. Examples of sustained-release matrices include polyesters, hydrogels [e.g. poly(2-hydroxyethyl-methacrylate) as described by Langer et al. *J. Biomed. Mater. Res.*, 15:167–277 (1981) and Langer, *Chem. Tec.,* 12:98–105 (1982) or poly(vinylalcohol)], polylactides (U.S. Pat. No. 3,779,919, EP 58,481), copolymers of L-glutamic acid and gamma ethyl-L-glutamate (Sidman et al.*Biopolymers,* 22:547–556 [1983]), non-degradable ethylene-vinyl acetate (Langer et al., supra), degradable lactic acid-glycolic acid copolymers such as the Luprom Depot™ (injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-release thrombopoietic protein compositions also include liposomally entrapped megakaryocytopoietic protein. Liposomes containing megakaryocytopoietic protein are prepared by methods knew per se: DE, 3,218,121; Epstein et al.*Proc. Natl. Acad. Sci. USA,* 82:3688–3698 [1985]; Hwang et al.*Proc. Natl. Acad. Sci. USA,* 77:4030–4034 [1980];EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal megakaryocytopoietic protein therapy.

A type of covalent modification of TPO or mpl ligand comprises linking the TPO polypeptide to one of a variety of nonproteinaceous polymers, e.g. polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337. TPO polypeptides covalently linked to the forgoing polymers are referred to herein as pegylated TPO.

It will be appreciated that some screening of the recovered TPO variant will be needed to select the optimal variant for binding to a mpl and having the immunological and/or biological activity defined above. One can screen for stability in recombinant cell culture or in plasma (e.g., against proteolytic cleavage), high affinity to a mpl member, oxidative stability, ability to be secreted in elevated yields, and the like. For example, a change in the immunological character of the TPO polypeptide, such as affinity for a given antibody, is measured by a competitive-type immunoassay. Other potential modifications of protein or polypeptide properties such as redox or thermal stability, hydrophobicity, or susceptibility to proteolytic degradation are assayed by methods well known in the art.

It will be understood that the present invention is directed to all associated aspects and embodiments embraced within the presently described invention. These and other details concerning them, and the present invention in general, form parts of the continued disclosure of the present invention in more detailed descriptive form infra.

BRIEF DESCRIPTION OF THE DRAWINGS

FIGS. 1A–1C—Animals rendered pancytopenic, by a combination of 5.0 Gy of γ-irradiation and carboplatin (1.2 mg), were injected subcutaneously with 0.1 μg rmTPO(335) for 1,2, 4, or 8 days. FIG. 1A shows the platelet response to the treatment regimens while FIGS. 1B and 1C represent the erythrocyte and leukocyte responses respectively over a 28 day period.

FIGS. 2A–2C—Animals rendered pancytopenic, by a combination of 5.0 Gy of γ-irradiation and carboplatin (1.2 mg), were injected subcutaneously with a single dose at various levels of rmTPO(335) 24 hours after the initiation of the experiment. FIG. 2A shows the platelet response to the treatment regimens while FIGS. 2B and 2C represent the erythrocyte and leukocyte responses respectively over a 28 day period.

FIGS. 3A–3B—Log-linear representations of the platelet (FIG. 3A) and erythrocyte (FIG. 3B) responses to single administrations of rmTPO(335) given either subcutaneously or intravenously in animals rendered pancytopenic by a combination of 5.0 Gy of γ-irradiation and carboplatin (1.2 mg). The cell numbers plotted are those measured on day 14 after initiation of the experiment. Φ is base line zero level.

FIGS. 4A–4C—Animals rendered pancytopenic, by a combination of 5.0 Gy of γ-irradiation and carboplatin (1.2 mg), were injected intravenously with a single dose at various levels of rmTPO(335) 24 hours after the initiation of the experiment. FIG. 4A shows the platelet response to the treatment regimens while FIGS. 4B and 4C represent the erythrocyte and leukocyte responses respectively over a 28 day period.

FIGS. 5A–5C—Animals rendered pancytopenic, by a combination of 5.0 Gy of γ-irradiation and carboplatin (1.2 mg), were injected subcutaneously with a single dose at 24 hours after the initiation of the experiment with various forms of rmTPO(153) conjugated to polyethylene glycol (peg) of either 20K or 40K molecular weight. FIG. 5A shows the platelet response to the treatment regimens while FIGS. 5B and 5C represent the erythrocyte and leukocyte responses respectively over a 28 day period.

FIGS. 6A–6C—Animals rendered pancytopenic, by a combination of 5.0 Gy of γ-irradiation and carboplatin (1.2 mg), were injected subcutaneously with a single dose at 24 hours after the initiation of the experiment with either rmTPO(335) or rmTPO(153) conjugated to polyethylene glycol (peg) of 40K molecular weight. FIG. 6A shows the platelet response to the treatment regimens while FIGS. 6B and 6C represent the erythrocyte and leukocyte responses respectively over a 28 day period.

FIGS. 7A–7C—Animals rendered pancytopenic, by a combination of 5.0 Gy of γ-irradiation and carboplatin (1.2 mg), were injected intravenously with a single dose at 24 hours after the initiation of the experiment with either rmTPO(335) or rmTPO(153) conjugated to polyethylene glycol (peg) of 40K molecular weight. FIG. 7A shows the platelet response to the treatment regimens while FIGS. 7B and 7C represent the erythrocyte and leukocyte responses respectively over a 28 day period.

DETAILED DESCRIPTION

Definitions

"Cytokine" is a generic term for proteins released by one cell population which act on another cell as intercellular mediators. Examples of such cytokines are lymphokines, monokines, and traditional polypeptide hormones. Included among the cytokines are growth hormone, insulin-like growth factors, human growth hormone including N-methionyl human growth hormone, bovine growth hormone, parathyroid hormone, thyroxine, insulin, proinsulin, relaxin, prorelaxin, glycoprotein hormones such as follicle stimulating hormone (FSH), thyroid stimulating hormone (TSH), and leutinizing hormone (LH), hematopoietic growth factor, hepatic growth factor, fibroblast growth factor, prolactin, placental lactogen, tumor necrosis factor (TNF-α and TNF-β), mullerian-inhibiting substance, mouse gonadotropin-associated peptide, inhibin, activin, vascular endothelial growth factor, integrin, nerve growth factors such as NGF-β, insulin-like growth factor-I and -II, erythropoietin (EPO), osteoinductive factors, interferons (IFN) such as interferon-α, -β and -γ, colony stimulating factors (CSFs) such as macrophage-CSF (M-CSF), granulocyte-macrophage-CSF (GM-CST), and granulocyte-CSF (G-CSF), interleukins (IL's) such as IL-1, IL-1α, IL-2, IL-3, IL-4, IL-5, IL-6, IL-7, IL-8, IL-9, IL-11, IL-12 and other polypeptide factors including LIF, SCF, FLT-3 ligand and kit-ligand (KL). As used herein the foregoing terms are meant to include proteins from natural sources or from recombinant cell culture. Similarly, the terms are intended to include biologically active equivalents; e.g., differing in amino acid sequence by one or more amino acids or in type or extent of glycosylation.

"Biologically active" when used in conjunction with thrombopoietin (TPO) means thrombopoietin or a thrombopoietic polypeptide that exhibits thrombopoietic activity or shares an effector function of the mpl ligand isolated from aplastic porcine plasma or expressed in recombinant cell culture. A principal known effector function of the mpl and stimulating the incorporation of labeled nucleotides ($^3$H-thymidine) into the DNA of IL-3 dependent Ba/F3 cells transfected with human mpl P. Another known effector function of the mpl ligand or polypeptide herein is the ability to stimulate the incorporation of $^{35}$S into circulating platelets in a mouse platelet rebound assay. Yet another known effector function of mpl ligand is the ability to stimulate in vitro human megakaryocytopoiesis that may be quantitated by using a radio labeled monoclonal antibody specific to the megakaryocyte glycoprotein $GPII_bIII_a$. "mpl ligand", mpl ligand polypeptide", "ML", "thrombopoietin" or "TPO" are used interchangeably herein and comprise any polypeptide that possesses the property of binding to mpl, a member of the cytokine receptor superfamily, and having a biological property of ML. An exemplary biological property is the ability to stimulate the incorporation of labeled nucleotides (e.g. $^3$H-thymidine) into the DNA of IL-3 dependent Ba/F3 cells transfected with human mpl. Another exemplary biological property is the ability to stimulate the incorporation of $^{35}$S into circulating platelets in a mouse platelet rebound assay. This definition encompasses the polypeptide isolated from a mpl ligand source such as aplastic porcine plasma described herein or from another source, such as another animal species, including humans or prepared by recombinant or synthetic methods and includes variant forms including functional derivatives, fragments, alleles, isoforms and analogues thereof.

A "mpl ligand fragment" or "TPO fragment" is a portion of a naturally occurring mature full length mpl ligand or TPO sequence having one or more amino acid residues or carbohydrate units deleted. The deleted amino acid residue(s) may occur anywhere in the peptide including at either the N-terminal or C-terminal end or internally. The fragment will share at least one biological property in common with mpl ligand. Mpl ligand fragments typically will have a consecutive sequence of at least 10, 15, 20, 25, 30 or 40 amino acid residues that are identical to the sequences of the mpl ligand isolated from a mammal including the ligand isolated from aplastic porcine plasma or the human or murine ligand, especially the EPO-domain thereof. Representative examples of N-terminal fragments are $hML_{153}$ orTPO ($Met^{-1}$ 1-153).

"TPO variants", "Mpl ligand variants" or "mpl ligand sequence variants" or the term "derivatives" in association with TPO, etc. as defined herein means a biologically active material as defined below having less than 100% sequence identity with the mpl ligand or TPO isolated from recombinant cell culture or aplastic porcine plasma or the human ligand. Ordinarily, a biologically active mpl ligand or TPO variant will have an amino acid sequence having at least about 70% amino acid sequence identity with the mpl ligand/TPO isolated from aplastic porcine plasma or the mature murine or human ligand or fragments thereof, preferably at least about 75%, more preferably at least about 80%, still more preferably at least about 85%, even more preferably at least about 90%, and most preferably at least about 95%.

A "chimeric" is a polypeptide comprising full length parent (TPO or mpl ligand) or one or more fragments thereof fused or bonded to a second heterologous polypeptide or one or more fragments thereof. The chimera will share at least one biological property in common. The second polypeptide will typically be a cytokine, immunoglobin or fragment thereof.

"Biological property" when used in conjunction with either the "mpl ligand" or "isolated mpl ligand" or "TPO" means having thrombopoietic activity or having an in vivo effector or antigenic function or activity that is directly or indirectly caused or performed by a mpl ligand or "TPO" (whether in its native or denatured conformation) or a fragment thereof. Effector functions include mpl binding and any carrier binding activity, agonism or antagonism of mpl, especially transduction of a proliferative signal including replication, DNA regulatory function, modulation of the biological activity of other cytokines, receptor (especially cytokine) activation, deactivation, up-or down regulation, cell growth or differentiation and the like. An antigenic function means possession of an epitope or antigenic site that is capable of cross-reacting with antibodies raised against the native mpl ligand or TPO. The principal antigenic function of a mpl ligand or TPO polypeptide is that it binds with an affinity of at least about $10^6$ l/mole to an antibody raised against the mpl ligand or TPO isolated from aplastic porcine plasma. Ordinarily, the polypeptide binds with an affinity of at least about $10^7$ l/mole. Most preferably, the antigenically active mpl ligand or TPO polypeptide is a polypeptide that binds to an antibody raised against the mpl ligand or TPO having one of the above described effector functions. The antibodies used to define "biological property" are rabbit polyclonal antibodies raised by formulating the mpl ligand or TPO isolated from recombinant cell culture or aplastic porcine plasma in Freund's complete adjuvant, subcutaneously injecting the formulation, and boosting the immune response by intraperitoneal injection of the formulation until the titer of mpl ligand or TPO antibody plateaus.

By the term "pegylated TPO polypeptides" or grammatical variations thereof, is meant a TPO polypeptide that has been covalently modified by linking the TPO polypeptide to one of a variety of non-proteinaceous polymers, for example, polyethylene glycol, polypropelene glycol or polyoxyalkylenes as set forth supra.

In humans, "thrombocytopenia" is defined as a condition wherein the platelet count is below about $150\times10^9$ per liter of blood.

"Thrombopoietic activity" is defined as biological activity that consists of accelerating the proliferation, differentiation and/or maturation of megakaryocytes or megakaryocyte precursors into the platelet producing form of these cells. This activity may be measured in various assays including an in vivo mouse platelet rebound synthesis assay, induction of platelet cell surface antigen assay as measured by an anti-platelet immunoassay (anti-$GPII_bIII_a$) for a human leukemia megakaryoblastic cell line (CMK), and induction of polyploidization in a megakaryoblastic cell line (DAMI).

"Thrombopoietin" (TPO) is defined as a compound having thrombopoietic activity or being capable of increasing serum platelet counts in a mammal. TPO is preferably capable of increasing endogenous platelet counts by at least 10%, more preferably by 50%, and most preferably capable of elevating platelet counts in a human to greater than about $150\times10^9$ per liter of blood. Reference is made as well to the other names extant in the literature for TPO, as discussed and referred to supra by reference as well to cited patent application documents.

The "mpl ligand" polypeptide or "TPO" of this invention preferably has at least 70% overall sequence identity with the amino acid sequence of the highly purified substantially homogeneous porcine mpl ligand polypeptide and at least 80% sequence identity with the "EPO-domain" of the porcine mpl ligand polypeptide. Optionally, the mpl ligand (TPO) of this invention is mature human mpl ligand (hML), or a variant or post-transcriptionally modified form thereof or a protein having about 80% sequence identity with mature human mpl ligand. Optionally, the mpl ligand variant is a fragment, especially an amino-terminus or "EPO-domain" fragment, of the mature human mpl ligand (hML). Preferably, the amino terminus fragment retains substantially all of the human ML sequence between the first and fourth cysteine residues but may contain substantial additions, deletions or substitutions outside that region. According to this embodiment, the fragment polypeptide may be represented by the formula:

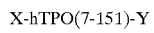

X-hTPO(7-151)-Y

Where hTPO(7-151) represents the human TPO (hML) amino acid sequence from $Cys^7$ through $Cys^{151}$ inclusive; X represents the amino group of $Cys^7$ or one or more of the amino-terminus amino acid residue(s) of the mature TPO or amino acid residue extensions thereto such as Met, Lys, Tyr or amino acid substitutions thereof such as arginine to lysine or leader sequences containing, for example, proteolytic cleavage sites (e.g. Factor Xa or thrombin); and Y represents the carboxy terminal group of $Cys^{151}$ or one or more carboxy-terminus amino acid residue(s) of the mature TPO or extensions thereto.

Methods of Making

Isolation of the Human mpl Ligand (TPO) Gene

Human genomic DNA clones of the TPO gene were isolated by screening a human genomic library in λ-Gem12 with pR45, under low stringency conditions or under high stringency conditions with a fragment corresponding to the 3' half of human cDNA coding for the mpl ligand. Two overlapping lambda clones spanning 35 kb were isolated. Two overlapping fragments (BamH1 and EcoRI) containing the entire TPO gene were subcloned and sequenced.

The structure of the human gene is composed of 6 exons within 7 kb of genomic DNA. The boundaries of all exon/intron junctions are consistent with the consensus motif established for mammalian genes (Shapiro, M. B. et al., Nucl. Acids. Res. 15:7155 [1987]). Exon 1 and exon 2 contain 5' untranslated sequence and the initial four amino acids of the signal peptide. The remainder of the secretory signal and the first 26 amino acids of the mature protein are encoded within exon 3. The entire carboxyl domain and 3' untranslated as well as ~50 amino acids of the erthropoietin-like domain are encoded within exon 6. The four amino acids involved in the deletion observed within hML-2 (hTPO-2) are encoded at the 5' end of exon 6.

Analysis of human genomic DNA by Southern blot indicated the gene for TPO is present in a single copy. The chromosomal location of the gene was determined by fluorescent in situ hybridization (FISH) which mapped to chromosome 3q27-28.

Expression and Purification of TPO from 293 Cells

Preparation and purification of ML or TPO from 293 cells is described in detail in Example 1. Briefly, cDNA corresponding to the TPO entire open reading frame was obtained by PCR using pRK5-hmpl I. The PCR product was purified and cloned between the restriction sites ClaI and XbaI of the plasmid pRK5tkneo.ORF (a vector coding for the entire open reading frame).

A second vector coding for the EPO homologous domain was generated the same but using different PCR primers to obtain the final construct called pRK5-tkneoEPO-D.

These two constructs were transfected into Human Embryonic Kidney cells by the $CaPO_4$ method and neomycin resistant clones were selected and allowed to grow to confluency. Expression of $ML_{153}$ or $ML_{332}$ in the conditioned media from these clones was assessed using the Ba/F3-mpl proliferation assay.

Purification of $rhML_{332}$ was conducted as described in Example 1. Briefly, 293-$rhML_{332}$ conditioned media was applied to a Blue-Sepharose (Pharmacia) column that was subsequently washed with a buffer containing 2M urea, the column was eluted with a buffer containing 2M urea and 1M NaCl. The Blue-Sepharose elution pool was then directly applied to a WGA-Sepharose column, washed with 10 column volumes of buffer containing 2M urea and 1M NaCl and eluted with the same buffer containing 0.5M N-acetyl-D-glucosamine. The WGA-Sepharose eluate was applied to a C4-HPLC column (Synchrom, Inc.) and eluted with a discontinuous propanol gradient. By SDS-PAGE the purified 293-$fhML_{332}$ migrates as a broad band in the 68–80 kDa region of the gel.

Purification of $rhML_{153}$ was also conducted as described in Example 1. Briefly, 293-$rhML_{153}$ conditioned media was resolved on Blue-Sepharose as described for $rhML_{332}$. The Blue Sepharose eluate was applied directly to a mpl-affinity column as described above. $RhML_{153}$ eluted from the mpl-affinity column was purified to homogeneity using a C4-HPLC column run under the same conditions used for $rhML_{332}$. By SDS-PAGE the purified $rhML_{153}$ resolves into 20 major and 2 minor bands with Mr of ~18,000–22,000.

Expression and Purification of TPO from Chinese Hamster Ovary (CHO) Cells

The expression vectors used to transfect CHO cells are designated: pSVI5.ID.LL.MLORF (full length of $TPO_{332}$), and pSVI5.ID.LL.MLEPO-D (truncated or $TPO_{153}$).

cDNA corresponding to the entire open reading frame of TPO was obtained by PCR. The PCR product was purified and cloned between two restriction sites (ClaI and SalI) of the plasmid pSVI5.ID.LL to obtain the vector pSVI5.ID.LL.MLORF. A second construct corresponding to the EPO homologous domain was generated the same way but using a different reverse primer (EPOD.Sal). The final construct for the vector coding for the EPO homologous domain of TPO is called pSVI5.ID.LL.MLEPO-D.

These two constructs were linearized with NotI and transfected into Chinese Hamster Ovary cells (CHO-DP12 cells, EP 307,247 published 15 Mar. 1989) by electroporation. $10^7$ cells were electroporated in a BRL electroporation apparatus (350 Volts, 330 mF, low capacitance) in the presence of 10, 25 or 50 mg of DNA as described (Andreason, G. L. J. Tissue Cult. Meth., 15:56 [1993]). The day following transfection, cells were split in DHFR selective media (High glucose DMEM-F12 50:50 without glycine, 2 mM glutamine, 2–5% dialyzed fetal calf serum). 10 to 15 days later individual colonies were transferred to 96 well plates and allowed to grow to confluency. Expression of $ML_{153}$ or $ML_{332}$ in the conditioned media from these clones was assessed using the Ba/F3-mpl proliferation assay.

The process for purifying and isolating TPO from harvested CHO cell culture fluid is described in Example 2. Briefly, harvested cell culture fluid (HCCF) is applied to a Blue Sepharose column (Pharmacia) at a ratio of approximately 100 L of HCCF per liter of resin. The column is then washed with 3 to 5 column volumes of buffer followed by 3 to 5 column volumes of a buffer containing 2.0M urea. TPO is then eluted with 3 to 5 column volumes of buffer containing both 2.0M urea and 1.0M NaCl.

The Blue Sepharose eluate pool containing TPO is then applied to a Wheat Germ Lectin Sepharose column (Pharmacia) equilibrated in the Blue Sepharose eluting buffer at a ratio of from 8 to 16 ml of Blue Sepharose eluate per ml of resin. The column is then washed with 2 to 3 column volumes of equilibration buffer. TPO is then eluted with 2 to 5 column volumes of a buffer containing 2.0M urea and 0.5M N-acetyl-D-glucosamine.

The Wheat Germ Lectin eluate containing TPO is then acidified and $C_{12}E_8$ is added to a final concentration of 0.04%. The resulting pool is applied to a C4 reversed phase column equilibrated in 01% TFA, 0.04% $C_{12}E_8$ at a load of approximately 0.2 to 0.5 mg protein per ml of resin.

The protein is eluted in a two phase linear gradient of acetonitrile containing 0.1% TFA and 0.04% $C_{12}E_8$ and a pool is made on the basis of SDS-PAGE.

The C4 Pool is then diluted and diafiltered versus approximately 6 volumes of buffer on an Amicon YM or like ultrafiltration membrane having a 10,000 to 30,000 Dalton molecular weight cut-off. The resulting diafiltrate may be then directly processed or further concentrated by ultrafiltration. The diafiltrate/concentrate is usually adjusted to a final concentration of 0.01% Tween-80.

All or a portion of the diafiltrate/concentrate equivalent to 2 to 5% of the calculated column volume is then applied to a Sephacryl S-300 HR column (Pharmacia) equilibrated in a buffer containing 0.01% Tween-80 and chromatographed. The TPO containing fractions which are free of aggregate and proteolytic degradation products are then pooled on the basis of SDS-PAGE. The resulting pool is filtered and stored at 2°–8° C.

Methods for Transforming and Inducing TPO Synthesis in a Microorganism and Isolating, Purifying and Refolding TPO Made Therein Construction of E. coli TPO expression vectors is described in detail in Example 3. Briefly, plasmids pMP21, pMP151, pMP41, pMP57 and pMP202 were all designed to express the first 155 amino acids of TPO downstream of a small leader which varies among the different constructs. The leaders provide primarily for high level translation initiation and rapid purification. The plasmids pMP210-1, -T8, -21, 22, -24, -25 are designed to express the first 153 amino acids of TPO downstream of an initiation methionine and differ only in the codon usage for the first 6 amino acids of TPO, while the plasmid pMP251 is a derivative of pMP210-1 in which the carboxy-terminal end of TPO is extended by two amino acids. All of the above plasmids will produce high levels of intracellular expression of TPO in *E. coli* upon induction of the tryptophan promoter (Yansure, D. G. et al., *Methods in Enzymology*, 185:54–60 (Goeddel, D. V., Ed.) Academic Press, San Diego [1990]). The plasmids pMP1 and pMP172 are intermediates in the construction of the above TPO intracellular expression plasmids.

The above TPO expression plasmids were used to transform the *E. coli* using the $CaCl_2$ heat shock method (Mandel, M. et al., *J. Mol. Biol*, 53:159–162, [1970]) and other procedures described in Example 3. Briefly, the transformed cells were grown first at 37° C. until the optical density (600 nm) of the culture reached approximately 2–3. The culture was then diluted and, after growth with aeration, acid was added. The culture was then allowed to continue growing with aeration for another 15 hours after which time the cells were harvested by centrifugation.

The isolation, purification and refolding procedures given below for production of biologically active, refolded human TPO or fragments thereof is described in Example 4 can be applied for the recovery of any TPO variant including N and C terminal extended forms. Other procedures suitable for refolding recombinant or synthetic TPO can be found in the following patents: Builder et al., U.S. Pat. No. 4,511,502; Jones et al., U.S. Pat. No. 4,512,922; Olson, U.S. Pat. No. 4,518,526 and Builder et al., U.S. Pat. No. 4,620,948; for a general description of the recovery and refolding process for a variety of recombinant proteins expressed in an insoluble form in *E. coli*.

Methods for Measurement of Thrombopoietic Activity

Thrombopoietic activity may be measured in various assays including the Ba/F3 mpl ligand assay. An in vivo mouse platelet rebound synthesis assay, induction of platelet cell surface antigen assay as measured by an anti-platelet immunoassay (anti-$GPII_bIII_a$) for a human leukemia megakaryoblastic cell line (CMK) (see Sato et al., *Brit. J. Heamatol.*, 72:184–190 [1989]) and induction of polyploidization in a megakaryoblastic cell line (DAMI) (see Ogura et al., *Blood*, 72(1):49–60 [1988]). Maturation of megakaryocytes from immature, largely non-DNA synthesizing cells, to morphologically identifiable megakaryocytes involves a process that includes appearance of cytoplasmic organelles, acquisition of membrane antigens ($GPII_bIII_a$), endoreplication and release of platelets as described in the background. A lineage specific promoter (i.e. the mpl ligand) of megakaryocyte maturation would be expected to induce at least some of these changes in immature megakaryocytes leading to platelet release and alleviation of thrombocytopenia. Thus, assays were designed to measure the emergence of these parameters in immature megakaryocyte cell lines, i.e., CMK and DAMI cells. The CMK assay measures the appearance of a specific platelet marker, $GPII_bIII_a$, and platelet shedding. The DAMI assay measures endoreplication since increases in ploidy are hallmarks of mature megakaryocytes. Recognizable megakaryocytes have ploidy values of 2N, 4N, 8N, 16N, 32N, etc. Finally, the in vivo mouse platelet rebound assay is useful in demonstrating that administration of the test compound (here the mpl ligand) results in elevation of platelet numbers.

Two additional in vitro assays have been developed to measure TPO activity. The first is a kinase receptor activation (KIRA) ELISA in which CHO cells are transfected with a mpl-Rse chimera and tyrosine phosphorylation of Rse is measured by ELISA after exposure of the mpl portion of the chimera to mpl ligand. The second is a receptor based ELISA in which ELISA plate coated rabbit anti-human IgG captures human chimeric receptor mpl-IgG which binds the mpl ligand being assayed. A biotinylated rabbit polyclonal antibody to mpl ligand ($TPO_{155}$) is used to detect bound mpl ligand which is measured using streptavidin-peroxidase.

Therapeutic Use of Thrombopoietin Materials

The biologically active thrombopoietic protein (TPO) may be used in a sterile pharmaceutical preparation or formulation to stimulate megakaryocytopoietic or thrombopoietic activity in patients suffering from thrombocytopenia due to impaired production, sequestration, or increased destruction of platelets. Thrombocytopenia-associated bone marrow hypoplasia (e.g. aplastic anemia following chemotherapy or bone marrow transplant) may be effectively treated with the compounds of this invention as well as disorders such as disseminated intravascular coagulation (DIC), immune thrombocytopenia (including HIV-induced ITP and non HIV-induced ITP), chronic idiopathic thrombocytopenia, congenital thrombocytopenia, myelodysplasia, and thrombotic thrombocytopenia. Additionally, these megakaryocytopoietic proteins may be useful in treating myeloproliferative thrombocytotic diseases as well as thrombocytosis from inflammatory conditions and in iron deficiency.

Preferred uses of the thrombocytopoietic protein (TPO) of this invention are in: myelotoxic chemotherapy for treatment of leukemia or solid tumors, myeloablative chemotherapy for autologous or allogeneic bone marrow transplant, myelodysplasia, idiopathic aplastic anemia, congenital thrombocytopenia, and immune thrombocytopenia.

Still other disorders usefully treated with the thrombopoietin proteins of this invention include defects or damage to platelets resulting from drugs, poisoning or activation on artificial surfaces. In these cases, the instant compounds may be employed to stimulate "shedding" or new "undamaged" platelets.

EXAMPLES

Example 1

Expression and Purification of TPO from 293 Cells Preparation of 293 Cell Expression Vectors A cDNA corresponding to the TPO entire open reading frame was obtained by PCR using the following oligonucleotides as primers:

TABLE 1

293 PCR Primers

Cla.FL.F:5' ATC GAT ATC GAT CAG CCA GAC ACC CCG GCC AG 3' (SEQ ID NO:1)
hmpII-R:5' GCT AGQ TCT AGA CAG GGA AGG GAG CTG TAC ATG AGA 3' (SEQ ID NO:2)

prk5-Hmpl was used as a template for the reaction in the presence of pfu DNA polymerase (Stratagene). Initial denaturation was for 7 min. at 94° C. followed by 25 cycles of amplification (1 min. at 94° C., 1 min. at 55° C. and 1 min. at 72° C.). Final extension was for 15 min. at 72° C. the PCR product was purified and cloned between the restriction sites ClaI and XbaI of the plasmid pRK5tkneo, a pRK5 derived vector modified to express a neomycin resistance gene under the control of the thymidine kinase promote, to obtain the vector pRK5tkneo.ORF. A second construct corresponding to the epo homologous domain was generated the same way but using Cla.FL.F as forward primer and the following reverse primer:

Arg. STOP.Xba: 5'TCT AGA TCT AGA TCA CCT GAC GCA GAG GGT GGA CC 3' (SEQ ID NO: 3)

The final construct is called pRK5-tkneoEPO-D. The sequence of both constructs was verified.

Transfection of Human Embryonic Kidney cells

These 2 constructs were transfected into Human Embryonic Kidney cells by the CaPO$_4$ method. 24 hours after transfection selection of neomycin resistant clones was started in the presence of 0.4 mg/ml G418. 10 to 15 days later individual colonies were transferred to 96 well plates and allowed to grow to confluency. Expression of ML$_{153}$ or ML$_{332}$ (TPO153 or TPO 332) in the conditioned media from these clones was assessed using the Ba/F3-mpl proliferation assay.

Purification of rhML$_{332}$ 392-rhML$_{332}$ conditioned media was applied to a Blue-sepharose (pharmacia) column that was equilibrated in 10 mM sodium phosphate pH 7.4 (buffer A). The column was subsequently washed with 10 column volumes each of buffer A and buffer A containing 2M urea. The column was then eluted with buffer A containing 2M urea and 1M NaCl. The blue-sepharose elution pool was then directly applied to a WGA-Sepharose column equilibrated in buffer A. The WGA-Sepharose column was then washed with 10 column volumes of buffer A containing 2M urea and 1M NaCl and eluted with the same buffer containing 0.5M N-acetyl-D-glucosamine. The WGA-Sepharose eluate was applied to a C4-HPLC column (Synchrom, Inc.) equilibrated in 0.1% TFA. The C4-HPLC column was eluted with discontinuous propanol gradient (0–25%, 25–35%, 35–70%). rhML$_{332}$ was found to elute in the 28–30% propanol region of the gradient, by SDS-PAGE the purified rhML$_{332}$ migrates as a broad band in the 68-8- kDa region of the gel.

Purification of rhML$_{153}$ 392-rhML$_{153}$ conditioned media was resolved on Blue-Sepharose as described For rhML$_{332}$. The Blue Sepharose eluate was applied directly to a mpl-affinity column as described above. RhML$_{153}$ eluted from the mpl-affinity column was purified to homogeneity using a C4-HPLC column run under the same conditions as described for rhML$_{332}$. By SDS-PAGE the purified rhML$_{153}$ resolves into 2 major and 2 minor bands with Mr of ~18,000–21,000.

Example 2

Expression and Purification of TPO from CHO

1. Description of CHO Expression Vectors

The expression vectors used in the electroporation protocols described below have been designated:

pSV15.ID.LL.MLORF (full length or hTPO$_{332}$), and
pSV15.ID.LL.MLEPO-D (truncated or hTPO$_{153}$).

2. Preparation of CHO Expression Vectors

A cDNA corresponding to the hTPO entire open reading frame was obtained by PCR using the oligonucleotide primes of the following Table.

CHO Expression Vector PCR Primers

Cla.FL.F2 5' ATC GAT ATC GAT AGC CAG ACA CCC CGG CCA G 3' (SEQ ID NO:4)
ORF.Sal 5' AGT CGA CGT CGA CGT CGG CAG TGT CTG AGA ACC 3' (SEQ ID NO:5)

PRK5-hmpl I was used as template for the reaction in the presence of pfu DNA polymerase (Stratagene). Initial denaturation was for 7 min. at 94° C. followed by 25 cycles of amplification (1 min. at 94° C., 1 min. at 55° C. and 1 min. at 72° C.). Final extension was for 15 min. at 72° C. The PCR product was purified and cloned between the restriction sites ClaI and SalI of the plasmid pSV15.ID.LL to obtain the vector pSV15.ID.LL.MLORF. A second construct corresponding to the EPO homologous domain was generated the same way but using Cla.FL.F2 as forward primer and the following reverse primer:

EPOD.Sal 5'AGT CGA CGT CGA CTC ACC TGA CGC AGA GGG TGG ACC 3' (SEQ ID NO:6)

The final construct is called pSV15.ID.LL.MLEPO-D. The sequence of both constructs was verified.

In essence, the coding sequences for the full length and truncated ligand were introduced into the multiple cloning site of the CHO expression vector pSV15.ID.LL. This vector contains the SV40 early promoter/enhancer region, a modified splice unit containing the mouse DHFR cDNA, a multiple cloning site for the introduction of the gene of interest (in this case the TPO sequences described) an SV40 polyadenylation signal and origin of replication and the beta-lactamase gene for plasmid selection and amplification in bacteria.

3. Methodology for Establishing Stable CHO Cell Lines Expressing Recombinant Human TPO$_{332}$ and TPO$_{153}$ a. Description of CHO parent cell line The host CHO (Chinese Hamster Ovary) cell line used for the expression of the TPO molecules described herein is known as CHO-DP12 (see EP 307,247 published 15 Mar. 1989). This mammalian cell line was clonally selected from a transfection of the parent line (CHO-K1 DUX-B11 (DHFR-)- obtained from Dr. Frank Lee of Stanford University with the permission of Dr. L. Chasin) with a vector expressing preproinsulin to obtain clones with reduced insulin requirements. These cells are also DHFR minus and clones can be selected for the presence of DHFR cDNA vector sequences by growth on medium devoid of nucleoside supplements (glycine, hypoxanthine, and thymidine). This selection system for stably expressing CHO cell lines is commonly used.

b. Transfection method (electroporation)

$TPO_{332}$ and $TPO_{153}$ expressing cell lines were generated by transfecting DP12 cells via electroporation (see e.g. Andreason, G. L. J. Tiss. Cult. Meth., 15, 56 (1993) with linearized pSVI5.ID.LL.MLORF or pSVI5.ID.LL.MLEPO-D plasmids respectively. Three (3) restriction enzyme reaction mixtures were set up for each plasmid cutting; 10 μg, 25 μg and 50 μg of the vector with the enzyme NOTI by standard molecular biology methods. This restriction site is found only once in the vector in the linearization region 3' and outside the TPO ligand transcription units (see FIG. 23). The 100 μl reactions were set up for overnight incubation at 37 degrees. The next day the mixes were phenol-chloroform-isoamyl alcohol (50:49:1) extracted one time and ethanol precipitated on dry ice for approximately one hour. The precipitate was then collected by a 15 minute microcentrifugation and dried. The linearized DNA was resuspended into 50 μl of Ham's DMEM-F12 1:1 medium supplemented with standard antibiotics and 2 mM glutamine.

Suspension growing DP12 cells were collected, washed one time in the medium described for resuspending the DNA and finally resuspended in the same medium at a concentration of $10^7$ cells per 750 μl. Aliquots of cells (750 μl) and each linearized DNA mix were incubated together at room temperature for one hour and then transferred to a BRL electroporation chamber. Each reaction mix was then electroporated in a standard BRL electroporation apparatus at 350 volts set at 330 μF and low capacitance. After electroporation, the cells were allowed to sit in the apparatus for 5 minutes and then on ice for an additional 10 minute incubation period. The electroporated cells were transferred to 60 mm cell culture dishes containing 5 ml of standard, complete growth medium for CHO cells (High glucose DMEM-F12 50:50 without glycine supplemented with 1×GHT, 2 mM glutamine, and 5% fetal calf serum) and grown overnight in a 5% CO2 cell culture incubator.

c. Selection and screening method

The next day, cells were trypsinized off the plates by standard methods and transferred to 150 mm tissue culture dishes containing DHFR selective medium (Ham's DMEM-F12, 1:1 medium described above supplemented with either 2% or 5% dialyzed fetal calf serum but devoid of glycine, hypoxanthine and thymidine this is the standard DHFR selection medium we use). Cells from each 60 mm dish were subsequently replated into 5/150 mm dishes. Cells were then incubated for 10 to 15 days(with one medium change) at 37 degrees/15% CO2 until clones began to appear and reached sizes amenable to transfer to 96 well dishes. Over a period of 4–5 days, cell lines were transferred to 96 well dishes using sterile yellow tips on a pipettman set at 50 ml. The cells were allowed to grow to confluency (usually 3–5 clays) and then the trays were trypsinized and 2 copies of the original tray were reproduced. Two of these copies were short term stored in the freezer with cells in each well diluted into 50 μl pf 10% FCS in DMSO. 5 day conditioned serum free medium samples were assayed from confluent wells in the third tray for TPO expression via the Ba/F cell based activity assay. The highest expressing clones based on this assay were revived from storage and scaled up to 2 confluent 150 mm T-flasks for transfer to the cell culture group for suspension adaptation, re-assay and banking.

d. Amplification Protocol

Several of the highest titer cell lines from the selection described above were subsequently put through a standard methotrexate amplification regime to generate higher titer clones. CHO cell clones are expanded and plated in 10 cm dishes at 4 concentrations of methotrexate (i.e 50 nM, 100 nM, 200 nM and 400 nM) at two or three cell numbers (105, 5×105, and 106 cells per dish). These cultures are then incubated at 37 degree/5% $CO_2$ until clones are established and amenable to transfer to 96 well dishes for further assay. Several high titer clones from this selection were again subjected to greater concentrations of methotrexate (i.e. 600 nM, 800 nM, 1000 nM and 1200 nM) and as before resistant clones are allowed to establish and then transferred to 96 well dishes and assayed.

4. Culturing Stable CHO Cell Lines Expressing Recombinant Human $TPO_{332}$ and $TPO_{153}$ Banked cells are thawed and the cell population is expanded by standard cell growth methods in either serum free or serum containing medium. After expansion to sufficient cell density, cells are washed to remove spent cell culture media. Cells are then cultured by any standard method including; batch, fed-batch or continuous culture at 25°–40° C., neutral pH, with a dissolved $O_2$ content of at least 5% until the constitutively secreted TPO is accumulated. Cell culture fluid is then separated from the cells by mechanical means such as centrifugation.

5. Purification of Recombinant Human TPO from CHO Culture Fluids

Harvested cell culture fluid (HCCF) is directly applied to a Blue Sepharose 6 Fast Flow column (Phamacia) equilibrated in 0.01M Na Phosphate pH7.4, 0.1 5M NaCl at a ratio of approximately 100 L of HCCF per liter of resin and at a linear flow rate of approximately 300 ml/hr/cm$^2$. The column is then washed with 3 to 5 column volumes of equilibration buffer followed by 3 to 5 column volumes of 0.01M Na Phosphate pH7.4, 2.0M urea. The TPO is then eluted with 3 to 5 column volumes of 0.01M Na Phosphate pH7.4, 2.0M urea, 1.0M NaCl.

The Blue Sepharose Pool containing TPO is then applied to a Wheat Germ, Lectin Sephlarose 6MB column (Pharmacia) equilibrated in 0.01M Na Phosphate pH7.4, 2.0M urea, and 1.0M NaCl at a ratio of from 8 to 16 ml of Blue Sepharose Pool per ml of resin at flow rate of approximately 50 ml/hr/cm$^2$. The column is then washed with 2 to 3 column volumes of equilibration buffer. The TPO is then eluted with 2 to 5 column volumes of 0.01M Na Phosphate pH7.4, 2.0M urea, 0.5M N-acetyl-D-glucosamine.

The Wheat Germ Lectin Pool is then adjusted to a final concentration of 0.04%/$C_{12}E_8$ and 0.1% trifluroacetic acid (TFA). The resulting pool is applied to a C4 reverse phase column (Vydac 214TP1022) equilibrated in 0.1% TFA, 0.04% $C_{12}E_8$ at a load of approximately 0.2 to 0.5 mg protein per ml of resin at a flow rate of 157 ml/hr/cm$^2$.

The protein is eluted in a two phase linear gradient of acetonitrile containing 0.1% TFA, 0.04% $C_{12}E_8$. The first phase is composed of a linear gradient from 0 to 30% acetonitrile in 15 minutes, the second phase is composed of a linear gradient from 30 to 60% acetonitrile in 60 minutes. The TPO elutes at approximately 50% acetonitrile. A pool is made on the basis of SDS-PAGE.

The C4 Pool is then diluted with 2 volumes of 0.01M Na Phosphate pH7.4, 0.15M NaCl and diafiltered versus approximately 6 volumes of 0.01M Na Phosphate pH7.4, 0.15M NaCl on an Amicon YM or like ultrafiltration membrane having a 10,000 to 30,000 Dalton molecular weight cut-off. The resulting diafiltrate may be then directly processed or further concentrated by ultrafiltration. The diafiltrate/concentrate is adjusted to a final concentration of 0.01% Tween-80.

All or a portion of the diafiltrate/concentrate equivalent to 2 to 5% of the calculated column volume is then applied to a Sephacryl S-300 HR column (Pharmacia) equilibrated in 0.01M Na Phosphate pH7.4, 0.15M NaCl, 0.01% Tween80 and chromatographed at a flow rate of approximately 17 ml/hr/cm$^2$. The TPO containing fractions which are free of aggregate and proteolytic degradation products are pooled on the basis of SDS-PAGE. The resulting pool is filtered on a 0.22$\mu$ filter, Millex-GV or like, and stored at 2°–8° C.

Example 3

Transformation and Induction of TPO Protein Synthesis In *E. coli*

1. Construction of *E. coli* TPO expression vectors

The plasmids pMP21, pMP151, pMP41, pMP57 and pMP202 are all designed to express the first 155 amino acids of TPO downstream of a small leader which varies among the different constructs. The leaders provide primarily for high level translation initiation and rapid purification. The plasmids pMP210-1, -T8, -21, -22, -24, -25 are designed to express the first 153 amino acids of TPO downstream of an initiation methionine and differ only in the codon usage for the first 6 amino acids of TPO, while the plasmid pMP251 is a derivative of pMP210-1 in which the carboxy terminal end of TPO is extended by two amino acids. All of the above plasmids will produce high levels of intracellular expression of TPO in *E. coli* upon induction of the tryptophan promoter (Yansura, D. G. et. al. *Methods in Enzymology* (Goeddel, D. V., Ed.) 185:54–60, Academic Press, San Diego [1990]). The plasmids pMP1 and pMP172 are intermediates in the construction of the above TPO intracellular expression plasmids.

(a) Plasmid pMP1

The plasmid pMP1 is a secretion vector for the first 155 amino acids of TPO, and was constructed by ligating together 5 fragments of DNA. The first of these was the vector pPho21 in which the small MluI-BamHI fragment had been removed. pPho21 is a derivative of phGH1 (Chang, C. N. et. al., *Gene* 55:189–196 (1987) in which the human growth hormone gene has been replaced with the *E. coli* phoA gene, and a MluI restriction site has been engineered into the coding sequence for the STII signal sequence at amino acids 20–21.

The next two fragments, a 258 base pair HinfI-PstI piece of DNA from pRK5-hmpI encoding TPO amino acids 19–103, and the following synthetic DNA encoding amino acids 1–18 5'-CGCGTATGCCAGCCCGGCTCCTCCTGCTTGTGAC CTCCGAGTCCTCAGTAAACTGCTT CGTG (SEQ ID NO: 7) ATACGGTCGGGCCGAGGAGGACGAA-CACTGGAGGCTCAGGAGTCATTTGACG AAGCACTGA-5' (SEQ ID NO:8) were preligated with T4-DNA ligase, and second cut with PstI. The fourth was a 152 base pair PstI-HaeIII fragment from pRK5hmpII encoding amino acids 104–155 of TPO. The last was a 412 base pair StuI-BamHI fragment from pdh108 containing the lambda to transcriptional terminator as previously described (Scholtissek, S. et. al., *NAR* 15:3185 [1987]).

(b) Plasmid pMP21

The plasmid pMP21 is designed to express the first 155 amino acids of TPO with the aid of a 13 amino acid leader comprising part of the STII signal sequence. It was constructed by ligating together three (3) DNA fragments, the first of these being the vector pVEG31 in which the small XbaI-SphI fragment had been removed. The vector pVEG31 is a derivative of pHGH207-1 (de Boer, H. A. et. al., in *Promoter Structure and Function* (Rodriguez, R. L. and Chamberlain, M. J., Ed), 462, Praeger, New York [1982]) in which the human growth hormone gene has been replaced by the gene for vascular endothelial growth factor (this identical vector fragment can be obtained from this latter plasmid).

The second part in the ligation was a synthetic DNA duplex with the following sequence:

5'-CTAGAATTATGAAAAAGAATATCGCATTTCTTC
TTAA (SEQ ID NO:9) TTAATACTTTTTCTTAT-
AGCGTAAAGAAGAATT
GCGC-5' (SEQ ID NO:10)

The last piece was a 1072 base pair MluI-SphI fragment from pMP1 encoding 155 amino acids of TPO.

(c) Plasmid pMP151

The plasmid pMP151 is designed to express the first 155 amino acids of TPO downstream of a leader comprising 7 amino acids of the STII signal sequence, 8 histidines, and a factor Xa cleavage site. pMP151 was constructed by ligating together three DNA fragments, the first of these being the previously de[]scribed vector pVEG31 from which the small XbaI-SphI fragment had been removed. The second was a synthetic DNA duplex with the following sequence:

5'-CTAGAATTATGAAAAAGAATATCGCATTTCATC
ACCATCACCATCACCATCACATCG
AAGGTCGTAGCC(SEQ ID NO:11)
TTAATACTTTTTCTTATAGCGTAAAG-
TAGTGGTAGTGGTAGTGGTAGTGTAGCT CCAGCAT-
5' (SEQ ID NO:12)

The last was a 1064 base pair BglI-SphI fragment from pMP11 encoding 154 amino acids of TPO. The plasmid pMP11 is identical to pMP1 with the exception of a few codon changes in the STII signal sequence (this fragment can be obtained from pMP1).

(d) Plasmid pMP202

The plasmid pMP202 is very similar to the expression vector pMP151 with the exception that the factor Xa cleavage site in the leader has been replaced with a thrombin cleavage site. As shown in FIG. 36, pMP202 was constructed by ligating together three DNA fragments. The first of these was the previously described pVEG31 in which the small XbaI-SphI fragment had been removed. The second was a synthetic DNA duplex with the following sequence:

5'-CTAGAATTATGAAAAAGAATATCGCATTTCATC
ACCATCACCATCACCATCACATCG AACCACG-
TAGCC (SEQ ID NO:13)
TTAATACTTTTTCTTATAGCGTAAAG-
TAGTGGTAGTGGTAGTGGTAGTGTAGCT
TGGTGCAT-5' (SEQ ID NO:14)

The last piece was a 1064 base pair BglI-SphI fragment from the previously described plasmid pMP11.

(e) Plasmid pMP172

The plasmid pMP172 is a secretion vector for the first 153 amino acids of TPO, and is an intermediate for the construction of pMP210. pMP172 was prepared by ligating together three DNA fragments, the first of which was the vector pLS321amB in which the small EcoRI-HindI section had been removed. The second was a 946 base pair EcoRI-HgaI fragment from the previously described plasmid pMP11. The last piece was a synthetic DNA duplex with the following sequence:

5'-TCCACCCTCTGCGTCAGGT (SEQ ID NO:15) GGAGACGCAGTCCATCGA-5' (SEQ ID NO:16)

(f) Plasmid pMP210

The plasmid pMP210 is designed to express the first 153 amino acids of TPO after a translational initiation methionine. This plasmid was actually made as a bank of plasmids in which the first 6 codons of TPO were randomized in the third position of each codon, and was constructed by the ligation of three DNA fragments. The first of these was the previously described vector pVEG31 in which the small XbaI-SphI fragment had been removed. The second was a synthetic DNA duplex shown below treated first with DNA polymerase (Klenow) followed by digestion with XbaI and HinI, and encoding the initiation methionine and the randomized first 6 codons of TPO.

5-'GCAGCAGTTCTAGAATTATGTCNCCNGCNCCN CCNGCNTGTGACCTCCGA ACACTGGAGGCT GTTCTCAGTAAA (SEQ ID NO:17) CAAGAGT-CATTTGACGAAGCACTGAGGGTACA GGAAG-5' (SEQ ID NO:18)

The third was a 890 base pair HinfI-SphI fragment from pMP172 encoding amino acids 19–153 of TPO.

The plasmid pMP210 bank of approximately 3700 clones was retransformed onto high tetracycline (50 µg/ml) LB plates to select out high translational initiation clones (Yansura, D. G. et al., Methods: *A Companion to Methods in Enzymology* 4:151–158 [1992]). Of the 8 colonies which came up on high tetracycline plates, five of the best in terms of TPO expression were subject to DNA sequencing.

(g) Plasmid pMP41

(g) Plasmid pMP41

The plasmid pMP41 is designed to express the first 155 amino acids of TPO fused to a leader consisting of 7 amino acids of the STII signal sequence following by a factor Xa cleavage site. The plasmid was constructed by ligating together three pieces of DNA, the first of which was the previously described vector pVEG31 in which the small XbaI-SphI fragment had been removed. The second was the following synthetic DNA duplex:

5'-CTAGAATTATGAAAAAGAATATCGCATTTATCG AAGGTCGTAGCC (SEQ ID NO:19) TTAATACTTTTTCTTATAGCGTAAATAGCTTCCA GCAT-5' (SEQ ID NO:20)

The last piece of the ligation was the 1064 base pair BgII-SphI fragment from the previously described plasmid pMP11.

(h) Plasmid pMP57

The plasmid pMP57 expresses the first 155 amino acids of TPO downstream of a leader consisting of 9 amino acids of the StII signal sequence and the dibasic site Lys-Arg. This dibasic site provides for a means of removing the leader with the protease ArgC. This plasmid was constructed by ligating together three DNA pieces. The first of these was the previously described vector pVEG31 in which the small XbaI-SphI fragment had been removed. The second was the following synthetic DNA duplex:

5-'CTAGAATTATGAAAAAGAATATCGCATTTCTTC TTAAACGTAGCC (SEQ ID NO:21) TTAATACTTTTTCTTATAGCGTAAAGAAGAATT TGCAT-5' (SEQ ID NO:22)

The last part of the ligation was the 1064 base pair BgiI-SphI fragment from the previously described plasmid pMP11.

(i) Plasmid pMP251

The plasmid pMP251 is a derivative of pMP210-1 in which two additional amino acids of TPO are included on the carboxy terminal end. This plasmid was constructed by ligating together two pieces of DNA, the first of these being the previously described pMP21 in which the small XbaI-ApaI fragment had been removed. The second part of the ligation was a 316 base pair XbaI-ApaI fragment from pMP210-1.

2. Transformation and Induction of *E. coli* with TPO expression vectors The above TPO expression plasmids were used to transform the *E. coli* strain 44C6 (w3110 tonAΔ rpoHts IonΔ cipΔ galE) using the CaCl2 heat shock method (Mandel, M. et al., *J. Mol. Biol.*, 53:159–162, [1970]). The transformed cells were grown first at 37° C. in LB media containing 50 pg/ml carbenicillin until the optical density (600 nm) of the culture reached approximately 2–3. The LB culture was then diluted 20× into M9 media containing 0.49% casamino acids (w/v) and 50 ~g/ml carbenicillin. After growth with aeration at 30° C. for 1 hour, indole-3-acrylic acid was added to a final concentration of 50 1 lg/ml. The culture was then allowed to continue growing at 30° C. with aeration for another 15 hours at which time the cells were harvested by centrifugation.

Example 4

Production of Biologically Active TPO (Met-1 1-153) in *E. coli*.

The procedures given below for production of biologically active, refolded TPO (Met$^{-1}$ 1-153) can be applied in analogy for the recovery of other TPO variants including N and C terminal extended forms.

A recovery of non-soluble TPO (Met$^{-1}$ 1-153)

*E. coli* cells expressing TPO (Met$^{-1}$ 1-153) encoded by the plasmid pMP210-1 are fermented as described above. Typically, about 100 g of cells are resuspended in 1 (10 volumes) of cell disruption buffer (10 mM Tris, 5 mM EDTA, pH 8) with a Polytron homogenizer and the cells centrifuged at 5000×g for 30 minutes. The washed cell pellet is again resuspended in 1 L cell disruption buffer with the Polytron homogenizer and the cell suspension is passed through an LH Cell Disrupter (LH Inceltech, Inc.) or through a Microfluidizer (Microfluidics International) according to the manufactures' instructions. The suspension is centrifuged at 5,000×g for 30 min. and resuspended and centrifuged a second time to make a washed refractile body pellet. The washed pellet is used immediately or stored frozen at --70° C.

B. Solubilization and purification of monomeric TPO Met$^{-1}$ 1-153)

The pellet from above is resuspended in 5 volumes by weight of 20 mM Tris, pH 8, with 6–8M guanidine and 25 mM DTT (dithiothreitol) and stirred for 1–3 hr., or overnight, at 4° C. to effect solubilization of the TPO protein. High concentrations of urea (6–8M) are also useful but generally result in lower yields compared to guanidine. After solubilization, the solution is centrifuged at 30,000×g for 30 min. to produce a clear supernatant containing denatured, monomeric TPO protein. The supernatant is then chromatographed on a Superdex 200 gel filtration column (Pharmacia, 2.6×60 cm) at a flow rate of 2 ml/min. and the protein eluted with 20 mM Na phosphate, pH 6.0, with 10 mM DTT Fractions containing monomeric, denatured TPO protein eluting between 160 and 200 ml are pooled. The TPO protein is further purified on a semi-preparative C4 reversed phase column (2×20 cm VYDAC). The sample is applied at 5 ml/min. to a column equilibrated in 0.1% TFA(trifluoroacetic acid) with 30% acetonitrile. The protein is eluted with a linear gradient of acetonitrile (30–60% in 60 min.). The purified reduced protein elutes at approximately 50% acetonitrile. This material is used for refolding to obtain biologically active TPO variant.

C. Generation of biologically active TPO (Met$^{-1}$ 1-153)

Approximately 20 mg of monomeric, reduced and denatured TPO protein in 40 ml 0.1% TFA/50% acetonitrile is diluted into 360 ml of refolding buffer containing optimally the following reagents:

50 mM Tris 0.3M NaCl 5 mM EDTA

2% CHAPS detergent

25% glycerol 5 mM oxidized glutathione 1 mM reduced glutathione pH adjusted to 8.3

After mixing, the refolding buffer is gently stirred at 4° C. for 12–48 hr to effect maximal refolding yields of the correct disulfide-bonded form of TPO (see below). The solution is then acidified with TFA to a final concentration of 0.2%, filtered through a 0.45 or 0.22 micron filter, and 1/10 volume of acetonitrile added. This solution is then pumped directly onto a C4 reversed phase column and the purified, refolded TPO (Met-1 1-153) eluted with the same gradient program as above. Refolded, biologically active TPO is eluted at approximately 45% acetonitrile under these conditions. Improper disulfide-bonded versions of TPO are eluted earlier. The final purified TPO (Met-1 1-153) is greater than 95% pure as assessed by SDS gels and analytical C4 reversed phase chromatography. For animal studies, the C4 purified material was dialyzed into physiologically compatible buffers. Isotonic buffers (10 mM Na acetate, pH 5.5, 10 mM Na succinate, pH 5.5 or 10 mM Na phosphate, pH 7.4) containing 150 mM NaCl and 0.01% Tween 80 were utilized.

Because of the high potency of TPO in the Ba/F3 assay (half maximal stimulation is achieved at approximately 3 pgml), it is possible to obtain biologically active material utilizing many different buffer, detergent and redox conditions. However, under most conditions only a small amount of properly folded material (<10%) is obtained. For commercial manufacturing processes, it is desirable to have refolding yields at least 10%, more preferably 30–50% and most preferably >50%. Many different detergents (Triton X-100, dodecyl-beta-maltoside, CHAPS, CHAPSO, SDS, sarkosyl, Tween 20 and Tween 80, Zwittergent 3–14 and others) were assessed for efficiency to support high refolding yields. Of these detergents, only the CHAPS family (CHAPS and CHAPSO) were found to be generally useful in the refolding reaction to limit protein aggregation and improper disulfide formation. Levels of CHAPS greater than 1% were most useful. Sodium chloride was required for best yields, with the optimal levels between 0.1M and 0.5M. The presence of EDTA (1–5 mM) limited the amount of metal-catalyzed oxidation (and aggregation) which was observed with some preparations. Glycerol concentrations of greater than 15% produced the optimal refolding conditions. For maximum yields, it was essential to have both oxidized and reduced glutathione or oxidized and reduced cysteine as the redox reagent pair. Generally higher yields were observed when the mole ratio of oxidized reagent is equal to or in excess over the reduced reagent member of the redox pair pH values between 7.5 and about 9 were optimal for refolding of these TPO variants. Organic solvents (e.g. ethanol, acetonitrile, methanol) were tolerated at concentrations of 10–15% or lower. Higher levels of organic solvents increased the amount of improperly folded forms. Tris and phosphate buffers were generally useful. Incubation at 4° C. also produced higher levels of properly folded TPO.

Refolding yields of 40–60% (based on the amount of reduced and denatured TPO used in the refolding reaction) are typical for preparations of TPO that have been purified through the first C4 step. Active material can be obtained when less pure preparations (e.g. directly after the Superdex 200 column or after the initial refractile body extraction) although the yields are less due to extensive precipitation and interference of non-TPO proteins during the TPO refolding process.

Since TPO (Met$^{-1}$ 1-153) contains 4 cysteine residues, it is possible to generate three different disulfide versions of this protein:

version 1: disulfides between cysteine residues 1–4 and 2–3 version 2: disulfides between cysteine residues 1–2 and 3–4 version 3: disulfides between cysteine residues 1–3 and 2–4.

During the initial exploration in determining refolding conditions, several different peaks containing the TPO protein were separated by C4 reversed phase chromatography. Only one of these peaks had significant biological activity as determined using the Ba/F3 assay. Subsequently, the refolding conditions were optimized to yield preferentially that version. Under these conditions, the misfolded versions are less than 10–20% of the total monomer TPO obtained.

The disulfide pattern for the biologically active TPO has been determined to be 1–4 and 2–3 by mass spectrometry and protein sequencing(i.e. version 1). Aliquots of the various C4-resolved peaks (5–10 nmoles) were digested with trypsin (1:25 mole ratio of trypsin to protein). The digestion mixture was analyzed by matrix assisted laser desorption mass spectrometry before and after reduction with DTT. After reduction, masses corresponding to most of the larger tryptic peptides of TPO were detected. In the un-reduced samples, some of these masses were missing and new masses were observed. The mass of the new peaks corresponded basically to the sum of the individual tryptic peptides involved in the disulfide pair. Thus it was possible to unequivocally assign the disulfide pattern of the refolded, recombinant, biologically active TPO to be 1–4 and 2–3. This is consistent with the known disulfide pattern of the related molecule erythropoietin.

D. Biological activity of recombinant, refolded TPO (met 1-153)

Refolded and purified TPO (Met$^{-1}$ 1-153) has activity in both in vitro and in vivo assays. In the Ba/F3 assay, half-maximal stimulation of thymidine incorporation into the Ba/F3 cells was achieved at 3.3 pg/ml (0.3 pM). In the mpl receptor-based ELISA, half-maximal activity occurred at 1.9 ng/ml (120 pM). In normal and myelosuppressed animals produced by near-lethal X-radiation, TPO (Met$^{-1}$ 1-153) was highly potent (activity was seen at doses as low as 30 ng/mouse) to stimulate the production of new platelets.

Example 5

Myelosuppressed (Carboplatin/Irradiation) Mouse Data

METHODS

ANIMALS

All animal studies were approved by the Institutional Care and Use Committee of Genentech Inc. Prior to the start of the experiment all animals were ear-tagged for identification and a base-line complete blood count (CBC) obtained. Groups of 10 female C57BL/6 mice were irradiated with 5.0 Gy of gamma irradiation from a $^{137}$CS source. Within 6 hours, the animals were given 1.2 mg carboplatin as a 200 μL intraperitoneal injection.

The following are the protocols and results using recombinant murine thrombopoietin (rmTPO) in a standard mouse model. It will be understood that one skilled in the art considers this model to be translatable into human beings. Human thrombopoietin has been tested in the same mouse model and was found to show relevant activity, albeit at a lesser level because of the species specificity. Therefore, the following protocol was chosen using the proper murine TPO counterpart for that species so that relevant effect could be demonstrated. Again, use of human TPO in the mouse protocol would provide similar results differing only in degree. Obviously the use of human TPO in human beings, another appropriate model comparison, must await FDA clinical testing approval.

PROCUREMENT OF BLOOD SAMPLES

Prior to the experiment and at time points throughout the study, 40 μL of blood was taken from the orbital sinus and immediately diluted into 10 mL of diluent to prevent clotting. The complete blood count (CBC) from each blood sample was measured on a Serrono Baker system 9018 blood analyzer within 60 min of collection. Only half of the animals in each dose group were bled on a given day; thus, each animal was bled on alternate time points.

TREATMENT REGIMENS

Experiment 1: In order to determine the response to recombinant murine thrombopoietin (rmTPO335aa) in animals rendered thrombocytopenic, groups of animals were treated for 1, 2, 4, or 8 consecutive days with 0.1 μg/day (5 μg/kg/day approx.). Treatment with rmTPO (335aa) was started 24 hours after the initiation of the model and was given as a daily 100 μL subcutaneous injection.

Experiment 2: In order to determine the nature of the dose-response relationship for rmTPO(335) in this model, animals were given a single injection of rmTPO (335) 24 hours after the initiation of the model. Groups of animals received one of 0.01, 0.03, 0.1 or 0.3 μg of rmTPO (335) as a single 100 μL subcutaneous injection. In order to compare two routes of administration, a contemporaneous experiment used 4 groups of animals receiving identical doses of rmTPO (335) but via an intravenous route (lateral tail vein).

Experiment 3: This series of experiments was done to compare the efficacy of various pegylated truncated rmTPO molecules [(rmTPO(153)] coupled to polyethylene glycol (PEG).

i. In this experiment thrombocytopenic animals were injected (0.1 μg subcutaneous) with one of the following pegylated rmTPO(153) molecules: no PEG, one 20K PEG or one 40K PEG.

ii. In the final experiment there was compared the effects of administering a singles 40K PEG rmTPO(153) molecule by giving 0.1 μg either subcutaneously or intravenously to animals rendered thrombocytopenic. rmTPO(335) (0.1 μg) was used as a positive control.

RESULTS

The combination of sublethal irradiation and carboplatin resulted in a reproducible response giving consistent thrombocytopenia in 100% of the animals. The nadir for the thrombocytopenia occurred at day 10 with a gradual recovery of platelet numbers by day 21 to day 28. Accompanying this thrombocytopenic was a pronounced anemia with the nadir occurring slightly later on day 14 to 17 and recovery to control red blood cell counts by day 28. White blood cell counts were also depleted during the course of the experiment.

Experiment 1: A single dose of 0.1 μg rmTPO(335) given 24 hours after the initiation of the model accelerated the recovery of platelet numbers in this murine model. This single administration of rmTPO(335) elevated the nadir of the response from $196\times10^3\pm33\times10^3/\mu L$ on day 10 to $434\times10^3\pm7\times10^3/\mu L$ on day 7. The initial rate of decline in the platelet numbers remained unchanged but the recovery phase was much more rapid with platelet numbers returning to normal by day 14 as opposed to day 21 in the control group. Some further improvement in the rate of recovery was seen by giving 0.1 μg/day on day 1 and day 2 but this was marginal. No further improvement could be seen by giving rmTPO(335) for 4 or 8 consecutive day (FIG. 1a). In addition to the accelerated recovery in platelet numbers, the anemia which develops in these animals was also attenuated by a single dose of rmTPO(335) given on day 1. As with the platelet counts, no further advantage could be gained by giving rmTPO(335) more than once (FIG. 1b). rmTPO(335) had no effect on the leukocytopenia that accompanies the falls in platelet and red blood cell counts. (FIG. 1c).

Experiment 2: The response to single subcutaneous doses of rmTPO(335) given 24 hours after the initiation of the model was dose dependent. The lowest dose tested (0.01 μg) had no effect on the platelet recovery compared to controls. However, the response is almost maximal when 0.03 μg was given (FIG. 2a). This extremely steep dose response curve is better appreciated when the platelet numbers on day 14 are plotted on a log-linear plot (FIG. 3a). A similar steep dose response is seen for erythrocyte repopulation in this model (FIG. 3b). Intravenous administration of rmTPO(335) gave a similar dose dependent response. However, the lowest dose tested (0.01 μg) was effective when given iv, (FIG. 4a) suggesting that the dose response curve is shifted to the left. This increase in potency is small since the shift is less than half an order of magnitude (FIG. 3a). What is more important is that both routes of administration have the comparable maxima (FIG. 3a). The subcutaneous and intravenous route of administration also augmented the recovery from the anemia in a dose-dependent fashion (FIGS. 2a, 3b, 4b). However, neither the subcutaneous nor the intravenous route of administration had an effect on the leukocytopenia over the dose range tested (FIGS. 2c, 4c).

Experiment 3:

i. Pegylation of the rmTPO(153) with either a single 20K PEG or a single 40K PEG had a greater effect on the platelet recovery than the un-pegylated molecule. Unlike the full-length molecule, neither of the pegylated rmTPO(153) molecules affected the nadir of the thrombocytopenia but greatly accelerated the recovery phase of the model when given as a single 0.1 μg sc. dose 24 hours after initiation of the model (FIG. 5a). This is very evident on day 14 when the platelet counts are $80\times10^3 \pm 15\times10^3/\mu L$, $268\times10^3\pm67\times10^3/\mu L$, $697\times10^3\pm297\times10^3/\mu L$ and $878\times10^3\pm31\times10^3/\mu L$ for controls, rmTPO(153) no PEG, rmTPO(153)+20K PEG and rmTPO(153)+40K PEG respectively (FIG. 5a). The same profile was also evident on the erythrocyte response (FIG. 5b). None of these rmTPO(153)-based molecules had any effect on the leukocytopenia in this model. (FIG. 5c).

ii. rmTPO(153)+40K PEG (0.1 μg) gave a consistent response when administered as either a single intravenous or subcutaneous injection. In this experiment, the subcutaneous route slightly altered the nadir on day 10 and returned platelets to control levels by day 14 as compared to day 28 in the control group (FIG. 6a). In the animals given the drug intravenously, there was a similar effect on the nadir and rate of recovery (FIG. 7a). The response to this 40K pegylated truncated rmTPO(153) molecule is almost identical to the response to the rmTPO(335) on both platelet and erythrocyte recovery when given either subcutaneously (FIG. 6b) or intravenously (FIG. 7b). As with all of the other experiments rmTPO(153)+40K PEG given either subcutaneously or intravenously had no effect on the circulating levels of white blood cells (FIGS. 6c, 7c). In parallel experiments, the use of 10K-pegylated versions of this molecule did not modify the response to rmTPO (153) on either platelet or erythrocyte repopulation.

The following are protocols and results using single-dose therapy with recombinant human thrombopoietin (rhTPO$_{332}$) in human patients receiving cytotoxic chemotherapy:

Single-dose therapy with recombinant human thrombopoietin (rhTPO) in patients receiving cytotoxic chemotherapy.

Preclinical models of intensive chemoradiotherapy demonstrated that a single dose of rhTPO raises the platelet nadir and shortens the period of severe thrombocytopenia. Interim results of two Phase I studies in which single doses of rhTPO were administered to cancer patients receiving chemotherapy are presented.

Patients and Methods

Both studies began with 21-day, pre-chemotherapy periods (cycle 0) for assessment of rhTPO safety and platelet response after single IV bolus injections of 0.3, 0.6, or 1.2 mcg/kg (3 patients per group in each study). Patients then received the same dose of rhTPO after chemotherapy in selected subsequent cycles. The first study population consisted of patients with advanced malignancies who received rhTPO the day following salvage thiotepa chemotherapy (65 mg/m$^2$ q28d) in each of two consecutive chemotherapy cycles. The second study included chemotherapy naive patients with sarcoma undergoing induction treatment with AI chemotherapy (doxorubicin 90 mg/m$^2$, 10 g/m$^2$ q2Id. Following cycle 0, patients in this study were monitored during the first chemotherapy cycle and received a single rhTPO injection the day following completion of chemotherapy (d5) during the second and subsequent cycles.

Results 14 patients have been treated to date. rhTPO was well tolerated with no reported serious adverse events attributed to study drug. Antibodies to rhTPO have not been observed. In cycle 0 the lowest (0.3 mcg/kg) dose was weakly active, with increased activity at higher doses as shown below.

| rhTPO dose (mcg/kg) | Patients N | Mean Baseline Patients (1 μl) (SD) | Median Maximum Platelet (1 μl) (Range) | Median % Increase |
|---|---|---|---|---|
| 0.3 | 7 | 339 (133) | 510 (277–628) | 40 |
| 0.6 | 5 | 235 (69) | 486 (386–509) | 103 |
| 1.2 | 2 | 203 (46) | 523 (437, 608) | 158 |

The maximum platelet count during cycle 0 occurred on median day 11 (range 7–14). No significant changes were found in WBC or HCT. FACS analysis of bone marrow showed increases in all CD34+ subsets in 2/2 patients following 0.6 mcg/kg. Increases in peripheral blood CD34+ cells were also seen in these patients, suggesting that TPO might have stem cell mobilizing activity. Dose calculation and post-chemotherapy treatment are ongoing.

Together these phase 1 studies suggest that single dose administration of rhTPO is safe and well tolerated. The 0.3, 0.6. and 1.2 mcg/kg. dose levels show increasing thrombopoietic activity. The ongoing treatment of patients at higher dose levels will test the hypotheses that a single dose of rhTPO is efficacious in ameliorating thrombocytopenia following intensive chemotherapy.

Concluding Remarks

The foregoing description details specific methods which can be employed to practice the present invention. Having detailed such specific methods, those skilled in the art will well enough know how to devise alternative reliable methods at arriving at the same information in using the fruits of the present invention. Thus, however detailed the foregoing may appear in test, it should not be construed as limiting the overall scope thereof; rather, the ambit of the present invention is to be determined only be the lawful construction of the appended claims. All documents cited herein are hereby expressly incorporated by reference.

I claim:

1. A method for treating a mammal having or at risk for thrombocytopenia due to impaired production of platelets by bone marrow, platelet sequestation in the spleen or increased platelet destruction in peripheral circulation, comprising administering to a mammal in need of such treatment a therapeutic dose on a single day only of a thrombopoietin which binds to and activates receptor mpl.

2. The method according to claim 1 wherein said thrombopoietin is administered in a single therapeutically effective dose.

3. The method according to claim 1 or claim 2 wherein said therapeutic dose ranges from about 1 to about 10 μg/kg.

4. The method according to claim 1 or claim 2 further comprising co-administering a therapeutically effective amount of an agent selected from the group consisting of a cytokine, colony stimulating factor and interleukin.

5. The method according to claim 4 wherein the agent is selected from the group consisting of Kit Ligand (KL), LIF, G-CSF, GM-CSF, M-CSF, EPO, FLT-3, IL-1, IL-2, IL-3, IL-5, IL-6, IL-7, IL-8, IL-9 and IL-11.

6. The method according to claim 1 or claim 2 wherein said thrombopoietin is administered intravenously.

7. The method according to claim 1 or claim 2 wherein said thrombopoietin is administered subcutaneously.

8. The method according to claim 1 or claim 2 wherein said thrombopoietin is administered in combination with a pharmaceutically acceptable carrier or excipient.

9. The method according to claim 8 wherein said carrier or excipient contains a chelating agent.

10. The method according to claim 9 wherein said chelating agent is EDTA.

11. The method according to claim 1 or claim 2 wherein said thrombopoietin is selected from the group consisting of:
   (a) human thrombopoietin (332);
   (b) a fragment of (a);
   (c) a variant polypeptide of (a);
   (d) a chimeric polypeptide comprising (a), (b) or (c); and
   (e) a pegylated form of (a), (b), (c) or (d).

12. The method according to claim 1 or claim 2 wherein said thrombopoietin is selected from the group consisting of
   a) a thrombopoietin isolated from a mammal;
   b) a thrombopoietin made by recombinant means; and
   c) a thrombopoietin made by synthetic means.

13. The method according to claim 1 or claim 2 wherein said thrombopoietin is selected from the group consisting of
   a) a human thrombopoietin; and
   b) a thrombopoietin non-immunogenic in a human.

14. The method according to claim 1 or claim 2 wherein said thrombopoietin is human thrombopoietin.

15. The method according to claim 14 wherein said thrombopoietin is human thrombopoietin (332).

16. The method according to claim 1 wherein said thrombopoietin is $rhTPO_{332}$.

17. The method of claim 1, wherein the mammal is thrombocytopenic.

18. The method of claim 1, wherein the mammal is at risk for thrombocytopenia.

19. A method for treating a mammal having or at risk for thrombocytopenia due to impaired production of platelets by bone marrow, platelet sequestration in the spleen or increased platelet destruction in peripheral circulation, comprising administering to a mammal in need of such treatment a therapeutic dose on a single day only of a thrombopoietin which binds to and activates receptor mpl wherein said thrombopoietin is represented by the formula:

X-hTPO(7-151)-Y where hTPO(7-151) represents the human TPO (hML) amino acid sequence from $Cys^7$ through $Cys^{151}$ inclusive; X represents the amino group of $Cys^7$ or one or more of the amino-terminus amino acid residue(s) of the mature TPO or amino acid residue extensions thereto or amino acid substitutions thereof; and Y represents the carboxy terminal group of $Cys^{151}$ or one or more carboxy-terminus amino acid residue(s) of the mature TPO or extensions thereto.

20. A method for treating a mammal having or at risk for thrombocytopenia due to impaired production of platelets by bone marrow, platelet sequestration in the spleen or increased platelet destruction in peripheral circulation, comprising administering to a mammal in need to such treatment a therapeutic dose on a single day only of a thrombopoietin which binds to and activates receptor mpl, wherein said thrombopoietin has at least one of the following activities:
   (a) the thrombopoietin induces incorporation of tritiated thymidine into the DNA of IL-3 dependent Ba/F3 cells transfected with human mpl,
   (b) the thrombopoietin induces GPIIbIIIa platelet cell surface antigen expression in a human leukemia megakaryoblastic cell line, or
   (c) the thrombopoietin induces polyploidization in a megakaryoblastic cell line.

21. The method of claim 20, wherein the thrombopoietin induces incorporation of tritiated thymidine into the DNA of IL-3 dependent Ba/F3 cells transfected with human mpl.

22. The method of claim 20, wherein the thrombopoietin induces GPIIbIIIa platelet cell surface antigen expression in a human leukemia megakaryoblastic cell line.

23. The method of claim 20, wherein the thrombopoietin induces polyploidization in a megakaryoblastic cell line.

* * * * *